United States Patent
Vedvick et al.

(10) Patent No.: US 10,172,930 B2
(45) Date of Patent: *Jan. 8, 2019

(54) VIRUS LIKE PARTICLE PURIFICATION

(71) Applicant: TAKEDA VACCINES, INC., Cambridge, MA (US)

(72) Inventors: Thomas S. Vedvick, Cambridge, MA (US); Bryan Steadman, Cambridge, MA (US); Charles Richardson, Cambridge, MA (US); Thomas R. Foubert, Cambridge, MA (US); Charles R. Petrie, Cambridge, MA (US)

(73) Assignee: TAKEDA VACCINES, INC., Cambridge, MA (US)

( * ) Notice: Subject to any disclaimer, the term of this patent is extended or adjusted under 35 U.S.C. 154(b) by 56 days.

This patent is subject to a terminal disclaimer.

(21) Appl. No.: 15/144,265

(22) Filed: May 2, 2016

(65) Prior Publication Data

US 2016/0317645 A1    Nov. 3, 2016

Related U.S. Application Data

(60) Division of application No. 13/914,331, filed on Jun. 10, 2013, now Pat. No. 9,359,410, which is a continuation of application No. 12/531,248, filed as application No. PCT/US2008/057072 on Mar. 14, 2008, now Pat. No. 8,481,693.

(60) Provisional application No. 60/906,821, filed on Mar. 14, 2007.

(51) Int. Cl.
*A61K 39/125*   (2006.01)
*A61K 39/12*    (2006.01)
*C12N 7/00*     (2006.01)
*C07K 1/18*     (2006.01)
*C07K 14/005*   (2006.01)

(52) U.S. Cl.
CPC ............ *A61K 39/12* (2013.01); *C07K 1/18* (2013.01); *C07K 14/005* (2013.01); *C12N 7/00* (2013.01); *C12N 2770/16023* (2013.01); *C12N 2770/16034* (2013.01); *C12N 2770/16051* (2013.01)

(58) Field of Classification Search
CPC .. A61K 2039/5258; C12N 2730/10123; C12N 2720/12323; C12N 2770/36123; C12N 2770/24123; C12N 2770/28123; C12N 2760/00023; C12N 2760/18523; C12N 2760/20023; C12N 2770/16011; C12N 2770/24023; C12N 2770/32423; C12N 2770/16034; C12N 2770/16023; C12N 2770/16022
See application file for complete search history.

(56) References Cited

U.S. PATENT DOCUMENTS

| | | | |
|---|---|---|---|
| 6,415,945 B1 | 7/2002 | McCarthy et al. | |
| 6,416,945 B1 | 7/2002 | McCarthy et al. | |
| 6,565,905 B1 | 5/2003 | Ito et al. | |
| 6,602,697 B1 | 8/2003 | Cook | |
| 7,041,500 B2 | 5/2006 | Robinson | |
| 7,067,638 B1 * | 6/2006 | Takeda | C07K 14/005 435/5 |
| 7,481,997 B1 * | 1/2009 | Hardy | C07K 16/10 424/93.1 |
| 7,527,801 B2 * | 5/2009 | Coit | A61K 39/12 424/184.1 |
| 7,575,753 B2 * | 8/2009 | Takeda | C07K 14/005 424/130.1 |
| 7,879,338 B2 * | 2/2011 | Hamilton | C12N 15/8258 424/216.1 |
| 7,955,603 B2 * | 6/2011 | Richardson | A61K 39/125 424/204.1 |
| 8,067,560 B2 * | 11/2011 | Takeda | C07K 14/005 435/320.1 |
| 8,119,145 B2 * | 2/2012 | Coit | A61K 39/12 424/184.1 |
| 8,124,104 B2 * | 2/2012 | Coit | A61K 39/12 424/184.1 |
| 8,277,819 B2 * | 10/2012 | Jiang | C07K 14/005 424/196.11 |
| 8,357,792 B2 * | 1/2013 | Takeda | C07K 14/005 424/216.1 |
| 8,431,116 B2 * | 4/2013 | Richardson | A61K 39/125 424/682 |
| 8,481,693 B2 * | 7/2013 | Vedvick | C12N 7/00 424/216.1 |
| 8,841,120 B2 * | 9/2014 | Richardson | A61K 39/12 435/320.1 |
| 8,980,275 B2 * | 3/2015 | Steadman | A61K 39/145 424/192.1 |
| 9,272,028 B2 * | 3/2016 | Richardson | A61K 39/125 |

(Continued)

FOREIGN PATENT DOCUMENTS

| CN | 102260651 A | 11/2011 |
|---|---|---|
| JP | H03-243861 A | 10/1991 |

(Continued)

OTHER PUBLICATIONS

Communcation for European Application No. 08782762 dated Aug. 12, 2011.

(Continued)

*Primary Examiner* — Bao Q Li
(74) *Attorney, Agent, or Firm* — Cooley LLP

(57) ABSTRACT

Methods for purifying human Calciviruses are disclosed, including Noroviruses and Sapoviruses.

11 Claims, 29 Drawing Sheets

(56) References Cited

U.S. PATENT DOCUMENTS

| | | | |
|---|---|---|---|
| 9,308,249 B2* | 4/2016 | Richardson | A61K 39/125 |
| 9,359,410 B2 | 6/2016 | Vedvick et al. | |
| 9,518,096 B2* | 12/2016 | Richardson | A61K 39/12 |
| 2001/0033837 A1 | 10/2001 | Metzner et al. | |
| 2004/0063188 A1 | 4/2004 | Robinson et al. | |
| 2007/0207526 A1 | 9/2007 | Coit et al. | |
| 2010/0150961 A1 | 6/2010 | Vedvick et al. | |
| 2012/0141529 A1 | 6/2012 | Coit et al. | |
| 2012/0156243 A1 | 6/2012 | Richardson et al. | |
| 2013/0344107 A1 | 12/2013 | Vedvick et al. | |
| 2014/0004145 A1 | 1/2014 | Taylor | |

FOREIGN PATENT DOCUMENTS

| | | | |
|---|---|---|---|
| JP | H10-500847 | 1/1998 | |
| JP | 2003-066021 A | 3/2003 | |
| WO | WO9615247 | 5/1996 | |
| WO | WO 1999/061475 A1 | 12/1999 | |
| WO | WO 2003/102132 A2 | 12/2003 | |
| WO | WO 2004/020971 A2 | 3/2004 | |
| WO | WO-2005032457 A2 * | 4/2005 | C07K 14/005 |
| WO | WO 2006/136566 | 12/2006 | |
| WO | WO-2006138514 A2 * | 12/2006 | C07K 14/005 |
| WO | WO 2008/113011 A2 | 9/2008 | |
| WO | WO 2009/080781 A1 | 7/2009 | |
| WO | WO 2011/012726 A2 | 2/2011 | |
| WO | WO 2012/040216 A1 | 3/2012 | |
| WO | WO 2013/192604 A1 | 12/2013 | |

OTHER PUBLICATIONS

Communcation for European Application No. 08782762 dated Mar. 30, 2012.
Decision to grant Patent in corresponding Japanese Application No. JP2009553820 dated Apr. 30, 2013.
Examination Report No. 1 in corresponding Australian Application No. 2008-224877 dated Jun. 25, 2012.
Sitch, Extended European Search Report for European Application No. 08782762 dated Jul. 26, 2011.
Young, International Search Report and Written Opinion for International Application No. PCT/US2008/57072 dated Oct. 1, 2008.
International Search Report PCT /US13/47249 dated Nov. 14, 2013.
Notice of Acceptance in corresponding Australian Application No. 2008-224877 dated Jul. 2, 2013.
Office Action in corresponding European Application No. 08782762 dated Mar. 25, 2014.
Office Action in corresponding Japanese Application No. 2009553820 dated Jan. 7, 2013.
Office Action for U.S. Appl. No. 12/531,248 dated Jan. 31, 2012.
Ausar,et al., "Conformational stability and disassembly of norwalk virus like particles: effect of pH and temperature," Bioi. Chem. 281:19478-19488 (2006).
Ball et al. "Oral Immunization with Recombinant Norwalk Virus-Like Particles Induces a Systemic and Mucosal Immune Response in Mice," Journal of Virology 72:1345-1353 (1998).
Ball et al., Recombinant Norwalk virus-like particles given orally to volunteers: phase I study. Gastroenterology 117:40-48 (1999).
Baric et al., "Expression and self-assembly of Norwalk virus capsid protein from venezuelan equine encephalitis virus replicons," J. Virol. 76(6):3023-3030 (2002).
Bertolotti-Ciarlet et al., "Structural requirements for the assembly of Norwalk virus-like particles," J. Virol. 76(8):4044-4055 (2002).
Cao, et al., "Structural basis for the recognition of blood group trisaccharides by norovirus," J. Virol. 81(11):5949-5957 (2007).
Chen et al.., "X-ray structure of a native calicivirus: structural insights into antigenic diversity and host specificity," Proc. Natl Acad. Sci. USA 103(21):8048-8053 (2006).
Cook et al., "Purification of virus-like particles ofrecombinant human papillomavirus type II major capsid protein L I from Saccharomyces cerevisiae," Protein Expr. Purif. 17(3):477-484 (1999).

Estes et al., "Norwalk Virus Vaccines: Challenges and Progress," The Journal of Infectious Disease 181(Suppl2):S367-373 (2000).
Fankhauser et al., "Molecular epidemiology of Norwalk-like viruses' in outbreaks of gastroenteritis in the United States," J. Infect. Dis. 178(6):1571-1578 (1998).
Herbst-Kralovetz, et al., "Norwalk virus-like particles as vaccines," Expert Rev. Vaccines 9(3): 299-307 (2010).
Jiang et al., "Expression, self-assembly, and antigenicity of the Norwalk virus capsid protein," J. Viral. 66(11):6527-6532 (1992).
Jiang et al, "Norwalk virus genome cloning and characterization," Science, 250:1580-1583 (1990).
Mason et al., "Expression of Norwalk virus capsid protein in transgenic tobacco and potato and its oral immunogenicity in mice," Proc. Nat! A cad. Sci. USA 93(11):5335-5340 (1996).
Nicollier-Jamot et al. Vaccine 22:1079-1086 (2004).
Oka et al., "Expression of sapovirus virus-like particles in mammalian cells," Arch. Virol., 151:399-404 (2006).
Pattenden et al., "Towards the preparative and large-scale precision manufacture of virus-like particles," Trends Biotechnol. 23(10): 523-529 (2005).
Prasad et al., "Structural studies of recombinant norwalk caps ids," J. Infect. Dis. 181(s2):S317-S321 (2000).
Rolland et al., "Purification of recombinant HBc antigen expressed in *Escherichia coli* and Pichia pastoris: comparison of size-exclusion chromatography and ultracentrifugation," J. Chromatog. B Biomed. Sci. App. 753(1): 51-65 (2001).
Antiseptics and Disinfectants for Infection Control, vol. 11, No. 1, pp. 28-31 (May 20, 2004).
Viruses vol. 52, No. 1, pp. 7-13 (Jun. 1, 2002).
Nippon Rinsho, vol. 60, No. 6, pp. 1222-1227 (Jun. 1, 2002).
Arch Virol, vol. 140, No. 6, pp. 1095-1108 (Jun. 21, 1995).
J. Med Virol., vol. 79, No. 1, pp. 74-83 (Jan. 2007).
Arch Virol., vol. 150, No. 7, pp. 1425-1431 (Jul. 2005).
Igaku no Ayumi, vol. 218, No. 10, pp. 868-876 (Sep. 2, 2006).
Almanza et al., "Self-Assembly of the Recombinant Capsid Protein of a Swine Norovirus into Virus-Like Particles and Evaluation of Monoclonal Antibodies Cross-Reactive with a Human Strain from Genogroup II." Journal of Clinical Microbiology (2008); 46(12): 3971-3979.
Antiseptics and Disinfectants for Infection Control, vol. 11, No. 1, pp. 28-31 (May 20, 2004) (with explanation).
Chen, Q. "Expression and purification of pharmaceutical proteins in plants." Biol Eng (2008); 1.4: 291-321.
Extended European Search Report for EP Application No. 13807804. 3, dated Nov. 3, 2015, 8 pages.
Huhti, L. et al. "A comparison of methods for purification and concentration of norovirus GII-4 capsid virus-like particles." Archives of Virology (2010); 155 (11): 1855-1858.
International Preliminary Report on Patentability for International Application No. PCT/US2008/57072 dated Sep. 15, 2009, 11 pages.
International Preliminary Report on Patentability for International Application No. PCT/US2013/047249, dated Dec. 23, 2014, 15 pages.
International Search Report and Written Opinion for International Application No. PCT/US2008/57072 dated Oct. 1, 2008, 13 pages.
International Search Report and Written Opinion for International Application No. PCT/US2013/047249, dated Nov. 14, 2013, 16 pages.
Koho, Tiia et al. "Purification of norovirus-like particles (VLPs) by ion exchange chromatography." Journal of Virological Methods (2012); 181(1): 6-11.
Lai, Huafang and Chen, Qiang. "Bioprocessing of plant-derived virus-like particles of Norwalk virus capsid protein under current Good Manufacture Practice regulations." Plant Cell Rep. (2012); 31(3): 573-584.
Parra, G. et al. "Immunogenicity and specificity of norovirus Consensus GII.4 virus-like particles in monovalent and bivalent vaccine formulations." Vaccine (2012); 30(24): 3580-3586.
Peixoto, C., et al. "Downstream processing of triple layered rotavirus like particles." Journal of Biotechnology (2007); 127.3: 452-461.

(56) References Cited

OTHER PUBLICATIONS

Chapter 4: Methods for Separation and Purification, Perfect Biotechnical Series, Notebook for Protein Experiment, Part I: Extraction and Separation/purification, Yodosha Co., Ltd., 1998, pp. 71-76 (Non English document).
Chapter 2: Methods for Purification of Proteins, 4. Purification by Column Chromatography, Separate Volume of Experimental Medicine: Protein Experiment Handbook—Summary of basic mechanisms and latest protocols on separation/purification, mass spectrometry, antibody preparation and molecular interaction analysis, Yodosha Co., Ltd., 2006, pp. 32-46 (Non English document).
Australian Patent Application No. 2008224877, Examination Report dated May 21, 2013, 2 pages.
Australian Patent Application No. 2013242822, Examination Report dated Aug. 27, 2015, 3 pages.
Australian Patent Application No. 2016269506, Examination Report dated Jan. 10, 2018, 4 pages.
Canadian Patent Application No. 2,683,977, Office Action dated Jul. 20, 2015, 3 pages.
Canadian Patent Application No. 2,683,977, Office Action dated Aug. 14, 2014, 4 pages.
Japanese Patent Application No. 2013-112580, Office Action dated Aug. 23, 2016, with English translation, 11 pages.
Japanese Patent Application No. 2013-112580, Office Action dated Oct. 21, 2014, with English translation, 6 pages.
Japanese Patent Application No. 2017-032171, Office Action dated Dec. 22, 2017, and English translation, 11 pages.
Korean Patent Application No. 10-2009-7021421, Office Action dated Apr. 27, 2015, with English translation, 9 pages.
Korean Patent Application No. 10-2009-7021421, Office Action dated Sep. 29, 2014, with English translation, 13 pages.
Korean Patent Application No. 10-2015-7020558, Office Action dated Feb. 13, 2017, with English translation, 7 pages.
Korean Patent Application No. 10-2015-7020558, Office Action dated Sep. 22, 2016, with English translation, 6 pages.
Korean Patent Application No. 10-2015-7020558, Office Action dated Nov. 4, 2015, with English translation, 7 pages.
Korean Patent Application No. 10-2016-7036031, Office Action dated Feb. 13, 2017, with English translation, 9 pages.
U.S. Appl. No. 12/531,248, Office Action dated Aug. 20, 2012, 10 pages.
U.S. Appl. No. 13/914,331, Office Action dated Aug. 14, 2015, 5 pages.
U.S. Appl. No. 13/914,331, Office Action dated Apr. 27, 2015, 5 pages.
Chinese Patent Application No. 201380043618.X, Office Action dated Sep. 27, 2017, with English translation, 14 pages.
Chinese Patent Application No. 201380043618.X, Office Action dated Mar. 22, 2017, with English translation, 14 pages.
Chinese Patent Application No. 201380043618.X, Office Action and Search Report dated Apr. 27, 2016, with English translation, 18 pages.
Japanese Patent Application No. 2015-518633, Office Action dated Mar. 28, 2017, with English translation, 18 pages.
Mexican Patent Application No. MX/a/2014/015842, Office Action dated Aug. 14, 2017, 4 pages. (Non English document).
Pakistani Patent Application No. 423/2013, Office Action dated Jun. 24, 2016, 1 page.
Taiwanese Patent Application No. 102122276, Office Action dated Aug. 30, 2017, with English translation, 7 pages.
U.S. Appl. No. 13/925,449, Office Action dated Sep. 8, 2017, 11 pages.
U.S. Appl. No. 13/925,449, Office Action dated Nov. 28, 2016, 11 pages.
U.S. Appl. No. 13/925,449, Office Action dated Jul. 14, 2016, 8 pages.
U.S. Appl. No. 13/925,449, Office Action dated Nov. 19, 2015, 7 pages.
U.S. Appl. No. 13/925,449, Office Action dated Jan. 23, 2018, 14 pages.
European Patent Application No. 13807804.3, Examination Report dated Feb. 5, 2018, 5 pages.
Japanese Patent Application No. 2015-518633, Office Action dated Jan. 31, 2018, with English translation, 27 pages.
Australian Patent Application No. 2013277959, Examination Report dated May 1, 2018, 16 pages.
Dika, et al., "Impact of Internal RNA on Aggregation and Electrokinetics of Viruses: Comparison between MS2 Phage and Corresponding Virus-Like Particles." Appl. Environ. Microbiol. (2011); 77 (14): 4939-4948.
Vicente, et al., "Large-scale production and purification of VLP-based vaccines." Journal of Invertebrate Pathology (2011); 107: S42-S48.
Japanese Patent Application No. 2017-032171, English translation of Office Action dated Sep. 6, 2018, 7 pages.

\* cited by examiner

| Lane | Sample ID |
|---|---|
| 1 | MW Std |
| 2 | Q100 Flow Through |
| 3 | Q100 20% Wash Fraction |
| 4 | Q100 20% Wash Fraction |
| 5 | Q100 40% Elution Fraction |
| 6 | Q100 40% Elution Fraction |
| 7 | Q100 40% Elution Fraction |
| 8 | Q100 40% Elution Fraction |
| 9 | Q100 100% Wash Fraction |
| 10 | Q100 100% Wash Fraction |
| 11 | VLP Extract |

VIRUS LIKE PARTICLE PURIFICATION

CROSS REFERENCE TO RELATED APPLICATIONS

This application is a divisional of U.S. application Ser. No. 13/914,331, filed Jun. 10, 2013, now issued as U.S. Pat. No. 9,359,410, which is a continuation of U.S. application Ser. No. 12/531,248, filed Feb. 26, 2010, now issued as U.S. Pat. No. 8,481,693, which is a 371 national stage application of International Patent Application No. PCT/US2008/057072, filed Mar. 14, 2008, which claims the benefit of priority of U.S. Provisional Application No. 60/906,821, filed Mar. 14, 2007, the entire content of each of which is incorporated herein by reference in its entirety.

STATEMENT OF GOVERNMENT SUPPORT

This invention was produced with government support from the US Army Medical Research and Material Command, under contract numbers DAMD17-01-C-0400 and W81XWH-05-C-0135. The government may have certain rights to the invention.

FIELD OF THE INVENTION

This application relates to methods for extracting and purifying virus like particles (VLPs) from biological sources. More particularly, it relates to methods for producing commercial grade VLPs at large scale. The methods employ a plurality of purification steps that yield purified VLPs.

BACKGROUND OF THE INVENTION

The human Caliciviruses Norovirus and Sapovirus are leading causes of acute, non-bacterial gastroenteritis. In contrast to Norovirus, Sapovirus is known to give infections mainly in infants and young children, however Sapovirus is increasingly found in the adult populations as well (Johansson et al., 2005, A nosocomial sapovirus-associated outbreak of gastroenteritis in adults. Scand J Infect Dis. 37(3):200-4). Noroviruses are non-cultivatable human Caliciviruses that have emerged as the single most important cause of epidemic outbreaks of nonbacterial gastroenteritis (Hardy, 1999, Clin Lab Med. 19(3):675-90). The clinical significance of Noroviruses was under-appreciated prior to the development of sensitive molecular diagnostic assays. The cloning of the prototype genogroup I Norwalk virus (NV) genome and the production of virus-like particles (VLPs) from a recombinant Baculovirus expression system led to the development of assays that revealed widespread Norovirus infections (Jiang et al. Norwalk Virus Genome Cloning and Characterization. *Science* 1990; 250: 1580-1583; Jiang et al. 1992, J. Virol. 66(11):6527-32).

Noroviruses and Sapoviruses are single-stranded, positive sense RNA viruses that contain a non-segmented RNA genome. The viral genome encodes three open reading frames, of which the latter two specify the production of the major capsid protein and a minor structural protein, respectively (Glass et al., The Epidemiology of Enteric Caliciviruses from Human: A Reassessment Using New Diagnostics. *J Infect Dis* 2000; 181 (Sup 2): S254-S261). When expressed at high levels in eukaryotic expression systems, the capsid protein of NV, and certain other Noroviruses and Sapoviruses, self-assembles into VLPs that structurally mimic native Norovirus virions. When viewed by transmission electron microscopy, the VLPs are morphologically indistinguishable from infectious virions isolated from human stool samples.

Although Norovirus and Sapovirus cannot be cultivated in vitro, due to the availability of VLPs and their ability to be produced in large quantities, considerable progress has been made in defining the antigenic and structural topography of the Norovirus capsid. VLPs preserve the authentic conformation of the viral capsid protein while lacking the infectious genetic material. Consequently, VLPs mimic the functional interactions of the virus with cellular receptors, thereby eliciting a strong host immune response while lacking the ability to reproduce or cause infection. In conjunction with the NIH, Baylor College of Medicine studied the humoral, mucosal and cellular immune responses to Norovirus VLPs in human volunteers in an academic, investigator-sponsored Phase I clinical trial. Orally administered VLPs were safe and immunogenic in healthy adults (Ball et al. 1999; Tacket et al. 2003). At other academic centers, preclinical experiments in animal models have demonstrated enhancement of immune responses to VLPs when administered intranasally with bacterial exotoxin adjuvants (Guerrero et al. 2001, Recombinant Norwalk Virus-like Particles Administered Intranasally to Mice Induce Systemic and Mucosal (Fecal and Vaginal) Immune Responses. *J Virol* 2001; 75: 9713; Nicollier-Jamot et al. 2004, Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. *Vaccine* 2004; 22:1079-1086; Periwal et al. 2003, Enhances Systemic and Mucosal Immune Responses to Recombinant Norwalk Virus-like Particle Vaccine. *Vaccine* 2003; 21: 376-385).

Small-scale methods for purifying Norovirus VLPs have been described in the literature. For example, Norwalk virus VLP purification by ultracentrifugation has been described (Jiang et al. 1990; 1992) and is commonly employed by the Norovirus investigators in the field. However, while VLPs purified by ultracentrifugation have been used in human clinical trials, the method is not suitable for producing commercial scale quantities of Calicivirus VLPs. Consequently, there remains a need to provide a scalable and efficient purification system capable of purifying VLPs from various biological sources.

SUMMARY OF THE INVENTION

Applicants have solved the need for scalable purification systems for Calicivirus VLPs by developing suitable chromatographic methods for the efficient purification of Calicivirus VLPs. The methods of the invention are amenable to scaling for commercial production of purified VLPs. Thus, the present invention relates to methods of purifying Calicivirus virus-like particles (VLPs) using chromatographic processes. The chromatographic process may utilize more than one chromatographic material and more than one mobile phase condition. The chromatographic materials and mobile phase conditions may be of different physical or chemical properties, making the chromatographic process orthogonal.

In some embodiments, the chromatographic materials and mobile phase conditions are selected to retain VLPs. In other embodiments, the chromatographic materials and mobile phase conditions are selected to pass through VLPs. In still other embodiments, the chromatographic materials and mobile phase conditions are selected to retain contaminants in VLP preparations. In yet other embodiments, the chromatographic materials and mobile phase conditions are selected to pass through contaminants in VLP preparations.

In some embodiments, among others, the chromatographic process of the invention is a multistep chromatographic process employing two or more chromatographic steps. The sequence of the multistep chromatographic process of the present invention may be designed to produce VLPs meeting preset specifications. For example, the purification method of the present invention may be used to purify VLPs to greater than about 70%, 80%, 90%, 95%, or greater than 99% purity.

In one embodiment, the sequence of the multistep chromatographic process is designed to control the resulting composition of VLPs. In another embodiment, the sequence of the multistep chromatographic process is designed to reduce contaminant levels to levels considered acceptable by regulatory agencies for pharmaceutical grade drug substance. For instance, the contaminant level of the host cell DNA content may be reduced to less than 1%. The contaminant level of the host cell protein content may be reduced to less than 5%. The sequence of the multistep chromatographic process is designed to make VLPs consistent with cGMP regulations and suitable for pharmaceutical testing in humans.

The present invention also encompasses a method of contacting a solution containing VLPs with a chromatographic material. In this regard, a cell lysate containing VLPs may be contacted with the chromatographic material wherein the cell lysate is filtered or purified by precipitation prior to contact with the chromatographic material. The solution or cell lysate may be centrifuged without a sucrose gradient. In one embodiment, a clarified solution containing VLPs is contacted with the chromatographic material. Alternatively, a VLP containing solution from one chromatographic step is contacted with another chromatographic material.

The VLP containing solution may be produced using recombinant methodologies. For example, the VLPs and VLP proteins may be produced in bacterial cells, insect cells, yeast cells, or mammalian cells.

In one embodiment, the present invention provides chromatographic material comprising chromatographic resin in solution, chromatographic resin in a column or chromatographic functionality incorporated into a membrane or onto a surface. The chromatographic material may be designed for the purification of proteins or nucleic acids. The chromatographic material may further comprise ion-exchange, affinity, hydrophobic interaction, mixed mode, reversed phase, size exclusion, and adsorption materials. The adsorption material may be a resin or membrane.

In one embodiment, the chromatographic material comprises a calcium phosphate based material. The calcium phosphate based material may be hydroxyapatite.

In another embodiment, the chromatographic material comprises an ion exchanger. The ion exchanger is a cation exchanger wherein the cation exchanger comprises sulfate, phosphate and carboxylate derivitized chromatographic materials. In another embodiment, the ion exchanger is an anion exchanger, wherein the ion exchanger comprises positively charged chromatographic material. The positively charged chromatographic material may be quaternary amine (Q) or diethylaminoethane (DEAE).

In yet another embodiment, the chromatographic material comprises a hydrophobic interaction material. The hydrophobic interaction material may comprise one or more functional groups selected from the group consisting of methyl, ethyl, t-butyl and phenyl. In one embodiment, the hydrophobic interaction chromatographic material is a methyl HIC resin.

In still another embodiment, the chromatographic material comprises a reverse phase material. The reversed phase material comprises C2, C4, C8 or C18 functionality. In another embodiment, the chromatographic material comprises an affinity chromatographic material. The affinity chromatographic material comprises antibodies, dry resins, and metals. The dry resin may be cibachrom blue or polymixin.

In one embodiment, the chromatographic material comprises a size exclusion material wherein the size exclusion material is a resin or membrane. The resin or membrane comprises pores of the same or different sizes.

The present invention also provides a method of purifying VLPs wherein the VLP-containing solution is adjusted to cause the retention of VLPs, with contaminating materials passing through the chromatographic material. In some embodiments, the pH of the VLP-containing solution may be adjusted with a buffer to more acidic values (e.g. pH less than 7). In other embodiments, the pH of the VLP-containing solution can be adjusted to more basic values (e.g. pH greater than 7). The buffer may comprise phosphate, carboxylate, sulfate, acetate, citrate, tris or bis tris. The buffer concentration may be in the range of about 10 to 1000 mM.

In one embodiment, the ionic strength of the VLP containing solution is adjusted. The ionic strength may be adjusted by anions and cations from the Hofmeister series such as ammonium sulfate. The ammonium sulfate concentration may be greater than about 100 milli molar, or about 1, 2, or 2.4 molar.

In another embodiment, the ionic strength is adjusted by the addition of a phosphate salt. In some embodiments, the phosphate salt is sodium phosphate. The sodium phosphate concentration may be in the range of about 10 to 500 mM. In one embodiment, the sodium phosphate concentration is about 100 mM.

In one embodiment of the invention, the pH of the chromatographic material is adjusted prior to VLP application by equilibration with a buffer to cause the retention of VLPs. The pH may be adjusted to acidic values (e.g. less than 7), basic values (e.g. greater than 7), or neutral values (e.g. equal to 7). The equilibration buffer may comprise phosphate, carboxylate, sulfate, acetate, citrate, tris or bis tris.

In another embodiment, the ionic strength of the chromatographic material is adjusted to cause retention of the VLPs. The adjustment may be achieved by the addition of salt. The salt may comprise cations and anions from the Hofmeister series such as ammonium sulfate. The concentration of ammonium sulfate may be greater than about 1, 2, or 2.4 molar.

In another embodiment, the ionic strength of the chromatographic material is adjusted by the addition of a phosphate salt. In some embodiments, the phosphate salt may be sodium phosphate. The sodium phosphate concentration may be in the range of about 10 to 500 mM. In one embodiment, the sodium phosphate concentration is about 100 mM.

In yet another embodiment, the organic solvent concentration of the VLP containing solution is adjusted to cause retention of VLPs.

The present invention further provides methods of purifying VLPs by selecting VLP containing solutions and chromatographic materials to cause retention of contaminating materials with the VLPs passing through the chromatographic resin. In so doing, the pH of the VLP containing solution may be adjusted with a buffer, e.g., the pH adjusted to less than 7 or greater than or equal to 7. The buffer may comprise phosphate, carboxylate, sulfate, acetate, citrate, tris or bis tris. In one embodiment, the buffer concentration is in the range of about 10 to 1000 mM.

In one embodiment, the ionic strength of the VLP containing solution is adjusted to cause retention of contaminating materials with the VLPs passing through the chromatographic material. This may be achieved by the addition of salt wherein the salt may comprise cations and anions from the Hofmeister series such as sodium phosphate. The sodium phosphate concentration may be in the range of about 10 to 500 mM. In one embodiment, the sodium phosphate concentration is about 100 mM.

In another embodiment, the pH of the chromatographic material is adjusted prior to VLP application by equilibration with a buffer to cause retention of contaminating materials with the VLPs passing through the chromatographic resin. The pH may be adjusted to less than 7 or greater than or equal to 7 with a buffer that may comprise phosphate, carboxylate, or sulfate.

In another embodiment, the ionic strength of the chromatographic material is adjusted prior to VLP application by equilibration with a buffer to cause retention of contaminating materials with the VLPs passing through the chromatographic resin. The ionic strength is adjusted by the addition of salt. The salt comprises cations and anions from the Hofmeister series such as sodium phosphate. In one embodiment, the sodium phosphate concentration is greater than about 10 mM.

In yet another embodiment, binding and elution of VLPs is controlled by the amount of organic solvent present in the mobile phase. The organic solvent concentration of the VLP containing solution may also be adjusted to cause retention of contaminating materials. The organic solvent can be an alcohol such as methanol, ethanol or propanol or other water miscible organic solvents such as acetonitrile.

The present invention further provides methods of purifying VLPs from Calicivirus virus-like particles (VLPs) such as Norovirus and Sapovirus VLPs. The Norovirus comprises Genogroup I, Genogroup II, Genogroup III, and Genogroup IV Noroviruses. Sapovirus comprises five Genogroups (I-V), among which only Genogroups I, II, IV, and V are known to infect humans (Farkas et al. 2004, Genetic diversity among sapoviruses. Arch Virol. 2004; 149:1309-23).

The present invention further provides a pharmaceutical agent prepared by the multistep chromatographic process. The pharmaceutical agent may be a vaccine such as a Norovirus vaccine.

The present invention further provides an analytical reagent prepared by the multistep chromatographic process described herein. The analytical reagent may be purified to a desired purification level, which can be used in a diagnostic assay or kit.

These and other embodiments of the invention will become apparent upon a full consideration of the invention presented below.

DETAILED DESCRIPTION OF THE INVENTION

Overview

Figure 1:
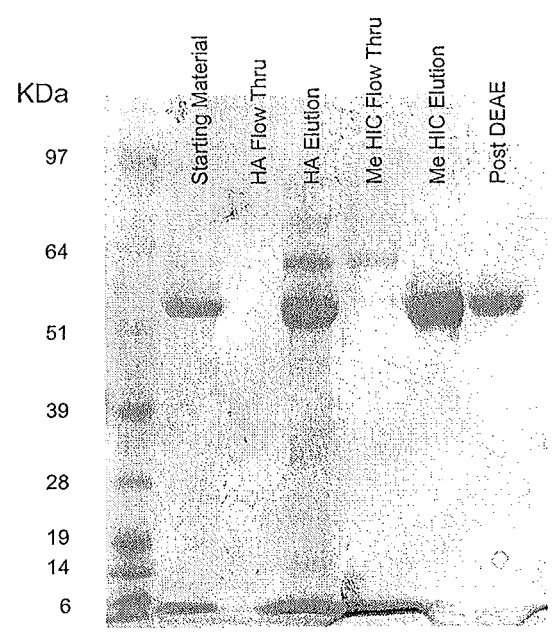
FIG. 1 is an example gel showing changes in VLP purity as a function of chromatographic step.

All publications and patent applications cited throughout this patent are incorporated by reference to the same extent as if each individual publication or patent/patent application is specifically and individually indicated to be incorporated by reference in their entirety.

Modifications and variations of this invention will be apparent to those skilled in the art. The specific embodiments described herein are offered by way of example only, and the invention is not to be construed as limited thereby.

The present invention relates to methods for the purification of Calicivirus virus-like particles (VLPs) including Norovirus VLPs and Sapovirus VLPs. By "Norovirus," "Norovirus (NOR)," "norovirus," and grammatical equivalents herein, are meant members of the genus Norovirus of the family Caliciviridae. In some embodiments, a Norovirus can include a group of related, positive-sense single-stranded RNA, nonenveloped viruses that can be infectious to human or non-human mammalian species. In some embodiments, a Norovirus can cause acute gastroenteritis in humans. Noroviruses also can be referred to as small round structured viruses (SRSVs) having a defined surface structure or ragged edge when viewed by electron microscopy. Included within the Noroviruses are at least four genogroups (GI-IV) defined by nucleic acid and amino acid sequences, which comprise 15 genetic clusters. The major genogroups are GI and GII. GIII and GIV are proposed but generally accepted. Representative of GIII is the bovine, Jena strain. GIV contains one virus, Alphatron, at this time. For a further description of Noroviruses see Vinje et al. J. Clin. Micro. 41:1423-1433 (2003). By "Norovirus" also herein is meant recombinant Norovirus virus-like particles (rNOR VLPs). In some embodiments, recombinant expression of at least the Norovirus capsid protein encoded by ORF2 in cells, e.g., from a baculovirus vector in Sf9 cells, can result in spontaneous self-assembly of the capsid protein into VLPs. In some embodiments, recombinant expression of at least the Norovirus proteins encoded by ORF2 and ORF3 in cells, e.g., from a baculovirus vector in Sf9 cells, can result in spontaneous self-assembly of the capsid protein into VLPs. VLPs are structurally similar to Noroviruses but lack the viral RNA genome and therefore are not infectious. Accordingly, "Norovirus" includes virions that can be infectious or non-infectious particles, which include defective and defective-interfering particles.

Non-limiting examples of Noroviruses include Norwalk virus (NV, GenBank M87661, $NP_{056821}$), Southampton virus (SHV, GenBank L07418), Desert Shield virus (DSV, U04469), Hesse virus (HSV), Chiba virus (CHV, GenBank AB042808), Hawaii virus (HV, GenBank U07611), Snow Mountain virus (SMV, GenBank U70059), Toronto virus (TV, Leite et al., Arch. Virol. 141:865-875), Bristol virus (BV), Jena virus (JV, AJ01099), Maryland virus (MV, AY032605), Seto virus (SV, GenBank AB031013), Camberwell (CV, AF145896), Lordsdale virus (LV, GenBank X86557), Grimsby virus (GrV, AJ004864), Mexico virus (MXV, GenBank U22498), Boxer (AF538679), C59 (AF435807), VA115 (AY038598), BUDS (AY660568), Houston virus (HoV, AY502023), MOH (AF397156), Parris Island (PiV; AY652979), VA387 (AY038600), VA207 (AY038599), and Operation Iraqi Freedom (OIF, AY675554). Non-limiting examples of Sapoviruses include Sapporo virus (SV), Houston/86 [U95643] (Hu/SLV/Hou/1986/US), Houston/90 [U95644] (Hu/SLV/Hou 27/1990/US), London 29845 [U95645] (Hu/SLV/Lon 29845/1992/UK), Manchester virus [X86560] (Hu/SLV/Man/1993/UK), Parkville virus [U73124] (Hu/SLV/Park/1994/US), Sapporo virus [U65427] (Hu/SLV/SV/1982/JP). Additional viral strains of Caliciviruses continue to be identified and are contemplated for use in the methods of the present invention (ICTVdB—The Universal Virus Database, version 4. http://www.ncbi.nlm.nih.gov/ICTVdb/ICTVdB/). The nucleic acid and corresponding amino acid sequences of each are all incorporated by reference in their entirety. In some embodiments, a cryptogram can be used for identification purposes and is organized: host species from which the virus was isolated/genus abbreviation/species abbreviation/strain name/year of occurrence/country of origin. (Green et al., Human Caliciviruses, in Fields Virology Vol. 1 841-874 (Knipe and Howley, editors-in-chief, 4th ed., Lippincott Williams & Wilkins 2001)). Representative examples of purifying Norwalk virus VLPs and Houston virus VLPs are discussed herein.

By "VLP preparation" is intended any solution containing VLPs, and other materials that are sought to be purified. The VLP preparation can be produced by a number of methods, including cultivation in a host cell in vitro including any one of batch, perfusion, or cell factory methods, or in vivo in an appropriate animal host. In the former instance, virally infected cells can be harvested, separated from the growth media, and the VLP protein either released into the media via a budding process or liberated by lysis of the cells and separation from cellular debris. In the latter instance, a tissue or organ harboring the virus can be removed and the VLP proteins also liberated by lysis of cells that comprise the tissue or organ, and separated from cellular/tissue debris.

As used herein, "virus-like particle(s) or VLPs" refer to a virus-like particle(s), fragment(s), or portion(s) thereof produced from a capsid protein coding sequence of Calicivirus and comprising antigenic characteristic(s) similar to those of infectious Calicivirus particles. VLPs can be any structural proteins wherein the structural proteins are encoded by one or more nucleic acid sequences. VLPs may include individual structural proteins, i.e., protein monomers, or dimers, or protein complexes spontaneously formed upon purification of recombinant structural proteins, i.e., self-assembling or intact VLPs, or aggregated VLPs. VLPs may also be in the form of capsid monomers, protein or peptide fragments of VLPs or capsid monomers, or aggregates or mixtures thereof. They may be produced using structural protein fragments or mutated forms thereof, e.g., structural proteins that have been modified by the addition, substitution or deletion of one or more amino acids. VLPs are morphologically and antigenically similar to authentic virions. VLPs may be produced in vivo, in suitable host cells, e.g., mammalian, yeast, bacterial, and insect host cells.

The present invention provides methods of large-scale purification of recombinant VLPs that were produced. The methods include preparing a solution, a cell lysate or culture supernatant from the host cell line then passing the lysate or culture supernatant over various combinations of chromatography materials or media. The host cell line may be cultured in Petri dishes, roller bottles, a bioreactor, or using another technique suitable for large-scale cell culture.

A skilled practitioner of this art will appreciate that other virus like particles may be purified using the process of the instant invention by adapting certain of its features as are appropriate to the VLP being purified. Suitable VLPs are those readily purified using multiple chromatographic steps in the purification process, chromatographic materials such as hydroxyapatite, hydrophobic interaction, ion exchange and size exclusion chromatographic materials.

A "bacterial cell" is herein defined to include prokaryotic cells that may be propagated in culture. The bacterial cell may act as a host cell for the recombinant expression of heterologous proteins. The bacterial cell may be transformed, transfected or infected with a vector for expression of a protein sequence inserted into the vector. Examples of suitable bacterial cells include, but are not limited to *E. coli, B. megaterium, B. subtilis* and *B. brevis* and various species of *Caulobacter, Staphylococcus*, and *Streptomyces*.

A "yeast cell" is herein defined to include the group consisting of small, unicellular organisms capable of growth and reproduction through budding or direct division (fission), or by growth as simple irregular filaments (mycelium). The yeast cell may be transformed or transfected with a heterologous vector for expression of a nucleic acid sequence inserted into the heterologous vector. An example of a yeast cell includes *Saccharomyces cerevisiae*, commonly used for transfection and expression of heterologous proteins.

A "mammalian cell culture" is herein defined to include the group of cells derived from a mammalian source capable of surviving ex vivo in a cell culture medium. The mammalian cell may be a primary cell, directly derived from a mammalian cell source. More typically, the mammalian cell in a mammalian cell culture will be immortalized, i.e. capable of growth and division through an indeterminate number of passages or divisions.

An "insect cell" is herein defined to include the group of cells derived from an insect source capable of surviving ex vivo from an insect host. The insect cell may be transformed, transfected or infected with a heterologous vector for expressions of a protein sequence inserted into the heterologous vector. Examples of insect cells include High Five™ cells, *Aedes albopictus* cells, *Drosophila melanogaster* cells, Sf9 insect cells and *Mamestra brassicae* cells.

"Lysis" refers to the process of opening virally infected cells by chemical, or physical means, or as part of the viral life cycle thereby allowing for the collection of VLPs.

By "porous chromatographic material" is meant virtually any type of material commonly used in the separation of molecules primarily based on their size, hydrophobicity and charge. As exemplified herein, "porous chromatographic material" includes dextran (e.g. Sephadex™ resins), or other porous materials that can be composed of a variety of materials including agarose, poly-styrene divinyl-benzene, polymethacrylate, silica, aliphatic acrylic polymers (e.g. Amberlite™ resins), with a variety of surface derivitizations (e.g., hydrophilic, ionic, hydrophobic, etc.).

As used herein, the term "precipitation" refers to the adjustment of solution conditions through the addition or removal of salt, the addition of organic solvent, the concentration of the protein containing solution or the adjustment of pH resulting in either the selective precipitation of molecules (VLPs or contaminant). Insoluble or precipitated material is then separated from the soluble material using a number of techniques such as centrifugation or filtration.

"Hydroxyapatite chromatography" refers to a method of purifying proteins that utilizes an insoluble hydroxylated calcium phosphate $Ca_{10}(PO_4)_6(OH)_2$, which forms both the matrix and ligand. Functional groups consist of pairs of positively charged calcium ions (C-sites) and clusters of negatively charged phosphate groups (P-sites). The interactions between hydroxyapatite and proteins are complex and multi-mode. In one method of interaction, however, positively charged amino groups on proteins associate with the negatively charged P-sites and protein carboxyl groups interact by coordination complexation to C-sites. Shepard, J. of Chromatography 891:93-98 (2000). Crystalline hydroxyapatite was the first type of hydroxyapatite used in chromatography, but it was limited by structural difficulties. Ceramic hydroxyapatite (cHA) chromatography was developed to overcome some of the difficulties associated with crystalline hydroxyapatite, such as limited flow rates. Ceramic hydroxyapatite has high durability, good protein binding capacity, and can be used at higher flow rates and pressures than crystalline hydroxyapatite. Vola et al., Bio-Techniques 14:650-655 (1993).

By "size exclusion chromatography" is meant a method for separating molecules using porous chromatographic material. Size exclusion chromatography can consist of one or more distinct types of porous chromatographic material used in a single step, or one or more distinct types of porous chromatographic material used in multiple separate steps. As used herein, an example of "size exclusion chromatography" where more than one porous chromatographic material is used is Amberlite™ XAD7HP and Sephadex™ G-50.

An "affinity material" is a solid-state material bound to a substrate or ligand, which in turn binds selectively to a protein of interest or a protein attached to an affinity tag. Upon binding, the protein of interest is retained within the column or other purifying apparatus, and may thus be separated from any impurities present in the VLP preparation. After washing of the affinity matrix, the protein of interest, may be eluted from the column or other apparatus in a substantially purified form. Examples of affinity matrices include chromatography medium, such as agarose, cellulose, Sepharose, Sephadex and other chromatography medium, polystyrene beads, magnetic beads, filters, membranes and other solid-state materials bound to ligands or substrates which bind to the affinity tag of choice.

As used herein, "to purify" a protein means to reduce to a given level of purity the amounts of foreign or objectionable elements, especially biological macromolecules such as proteins or DNA, that may be present in a sample of the protein. For instance, the methods of the present invention may be used to purify VLPs for greater than about 70%, 80%, 90%, 95% or greater than 99% purity. The presence of foreign proteins may be assayed by any appropriate method including, but not limited to gel electrophoresis and staining or western blot analysis, HPLC and/or ELISA assay. The presence of DNA may be assayed by any appropriate method including gel electrophoresis and staining, DNA binding proteins and/or assays employing polymerase chain reaction.

As used herein, the terms "chromatographic material," "chromatographic medium," "chromatographic matrix," and "chromatographic resin" and their grammatical equivalents are used interchangeably throughout the specification.

Description of the Purification Procedure

The present invention relates to the purification of virus-like particles (VLP) from biological source materials. More specifically it relates to the use of chromatographic methods as a means to remove impurities and contaminants that may be detrimental to the recombinant VLP integrity or its subsequent use.

The disclosed invention contemplates using a single or plurality of chromatographic step(s) in order to purify VLPs from a biological source. Different chromatographic materials, used in varying orders and combinations, are contemplated by the present invention. The chromatographic step(s) may utilize more than one chromatographic material and more than one mobile phase condition. The chromatographic materials and mobile phase conditions may be of different physical or chemical properties, and thus are orthogonal.

Chromatographic materials include, but are not limited to, ion-exchange, affinity, hydrophobic interaction, mixed mode, reversed phase, size exclusion, and adsorption materials. The invention also contemplates many support medium, including agarose, cellulose, silica, and poly (stryrene-divinylbenzene) (PSDVB). In addition, multiple chromatographic methods can be used including conventional chromatography, HPLC (High Performance Liquid Chromatography or High pressure Liquid Chromatography), or perfusion chromatography. One skilled in the art will also appreciate that the size of the column (i.e., diameter and length) will depend on several factors such as the volume of material to be loaded, the concentration of VLPs to be purified, and the desired resolution or purity.

Cell Lysate Preparation

The practice of the invention employs techniques of molecular biology, protein analysis and microbiology, which are within the skills of a practitioner in the art. Such techniques are explained fully in, e.g., Current Protocols in Molecular Biology, Ausubel et al., eds., John Wiley & Sons, New York, 1995.

VLPs can be purified from cell lysates prepared from a number of biological sources including cell lines, tissues, etc. Often VLPs will be purified from a cell lysate preparation made from virus infected cells, where the cells have been grown using cell culture methods. The VLP containing cell lysates may be produced using recombinant methodologies. For example, the VLPs and VLP proteins may be produced in bacterial cells, insect cells, yeast cells, or mammalian cells. For example, Norovirus VLPs can be isolated from Baculovirus-infected SF9 cells, etc. Cells may be infected at high multiplicity of infection in order to optimize yield.

Any method suitable for releasing VLP proteins from infected cells may be utilized to prepare a cell lysate containing VLP. VLP protein may also be released into the growth media via a budding process. VLPs may be recovered via separation from the media and cellular debris or released from infected cells using techniques known in the art. The methods of lysing virally infected cells may include using hypotonic solution, hypertonic solution, sonication, pressure, or a detergent. In one embodiment, the technique is to use a detergent. In another embodiment, depending on the amount of DNA and RNA in the sample, the technique is to also use a nuclease in combination with a detergent.

Numerous detergents are available to solubilize cells, including non-ionic or ionic detergents. An enzymatic agent may be used to treat the cell lysate consisting of one or more enzymes, preferably an RNAse and/or a DNAse, or a mixture of endonucleases as would be known to the ordinarily skilled artisan. It is well known that nucleic acids may adhere to cellular material which can interfere with the invention chromatographic purification scheme by causing cellular or viral aggregation, resulting in little if any VLPs being recovered.

Clarification

Prior to the clarification step, the cell lysate preparation following treatment with detergent, or if preferred, detergent and nuclease, may be treated to remove large particulate matter. This can be accomplished by a number of procedures including low speed centrifugation, or filtration. The type of filter or membrane used (i.e. composition and pore size) is within the knowledge of the skilled practitioner of the art to purify particular VLPs.

One embodiment of the invention involves clarification by precipitation. The desired VLP proteins may be recovered from the cell lysate or culture supernatant by the use of precipitation techniques well known to those in the art, such as by the use of protein precipitation agents including, but not exclusively, PEG, sodium sulfate, ammonium sulfate, glycine or temperature. The precipitation is preferably carried out with carefully selected concentrations of the chemical agents as this reduces co-precipitation of contaminating proteins. Precipitated proteins are then separated from soluble materials by filtration or by centrifugation. In one embodiment of the invention, the VLPs are precipitated by reducing the ionic strength of the solution through the addition of deionized water. In another embodiment, VLPs are precipitated by the addition of ammonium sulfate. The precipitated VLPs are then collected using a low speed centrifugation and resuspended in buffer Another embodiment of the invention may involve clarification using porous chromatographic materials. In purifying VLP from certain cell lysates and depending on the amount of cellular aggregates present, it may be desirable to use a single porous chromatographic material to perform size exclusion chromatography. In these instances it may be sufficient to employ a pre-clarification (i.e. filtration) step, followed by size exclusion chromatography using a single porous chromatographic material preferably made of dextran, and more preferably certain Sephadex™ resins. Generally, a cell lysate or cell culture supernatant, obtained by means that are well known in the art, is subject to clarification.

In one embodiment, the present invention provides chromatographic material comprising chromatographic resin in solution, chromatographic resin in a column or chromatographic functionality incorporated into a membrane or onto a surface. By "membrane" is meant virtually any type of material commonly used in the separation of molecules primarily based on their size. As exemplified herein, "membrane' includes filters or other porous materials that can be used for molecule separation.

The chromatographic material may be designed for the purification of proteins or nucleic acids. The chromatographic material may further comprise ion-exchange, affinity, hydrophobic interaction, mixed mode, reversed phase, size exclusion, and adsorption materials. Exemplary chromatographic materials of the present invention are described in more detail below. It should be understood that the chromatographic materials are provided for the purpose of illustration only and the invention should in no way be construed as being limited to these chromatographic materials or steps but rather should be construed to encompass any and all chromatographic materials or steps that can be used for protein or nucleic acid purification in general and VLP purification in particular.

The chromatographic methods discussed below can be run as individual steps, or sequentially, or in tandem. By "in tandem" is meant that an eluate from one chromatography is directly applied to the next chromatography without an intervening eluate collection step. Alternatively, fractions of an eluate may be pooled and collected prior to being applied to the next chromatography.

Hydroxyapatite Chromatographic Material

In some embodiments, the chromatographic material comprises a calcium phosphate based material. The calcium phosphate based material may be hydroxyapatite. Various hydroxyapatite chromatographic materials or resins are available commercially, and any available form of the material can be used in the practice of this invention. In one embodiment of the invention, the hydroxyapatite is in a crystalline form. Hydroxyapatites for use in this invention may be those that are agglomerated to form particles and sintered at high temperatures into a stable porous ceramic mass.

The particle size of the hydroxyapatite may vary widely, but a typical particle size ranges from 1 μm to 1,000 μm in diameter, and may be from 10 μm to 100 μm. In one embodiment of the invention, the particle size is 20 μm. In another embodiment of the invention, the particle size is 40 μm. In yet another embodiment of the invention, the particle size is 80 μm.

This invention may be used with hydroxyapatite resin that is loose, packed in a column, or in a continuous annular chromatograph. In one embodiment of the invention, ceramic hydroxyapatite resin is packed in a column. The choice of column dimensions can be determined by the skilled artisan. In one embodiment of the invention, a column diameter of at least 0.5 cm with a bed height of about 20 cm may be used for small scale purification. In an additional embodiment of the invention, a column diameter of from about 35 cm to about 60 cm may be used. In yet another embodiment of the invention, a column diameter of from 60 cm to 85 cm may be used.

Eluate from the hydroxyapatite column containing VLPs may be pooled and applied to another chromatographic resin such as the hydrophobic interaction chromatographic resin.

Hydrophobic Interaction Chromatographic Material

In some embodiments, the chromatographic material comprises a hydrophobic interaction material. The hydrophobic interaction material may comprise one or more functional groups selected from the group consisting of methyl, ethyl, t-butyl and phenyl.

Hydrophobic interaction chromatography ("HIC") is a valuable technique for the separation of proteins under high salt conditions (see, generally, HPLC of Biological Macromolecules. Methods and Applications, Gooding, K. M. et al., Eds., Marcel Dekker, Inc. (1990)). With regard to proteins, HIC separation is based on the interactions of the hydrophobic amino acid residues of the protein with immobilized hydrophobic moieties immobilized to a chromatographic support. The immobilized hydrophobic moieties may be selected from a broad range of alkyl and aryl groups. PEG is an immobilized moiety that is commonly used in HIC chromatography. The hydrophobicity of the moiety increases with increasing alkyl length. The protein is adsorbed to the column in high salt (1-3M $NH_4(SO_4)_2$), and is eluted by lowering the ionic strength. Methods of conducting HIC are described by Cameron, G. W. et al. (Meth. Molec. Cell. Biol. 4:184-188 (1993)), Raymond, J. et al. (J. Chromatog. 212:199-209 (1981)), Ochoa, J. I. (Biochimie 60:1-15 (1978)), Roggenbuck, D. et al. (J. Immunol. Meth. 167:207-218 (1994)), Michaelson, S. et al. (Pol. J. Food Nutr. Sci. 3/44:5-44 (1994), Rippel, G. et al. (J. Chromatog. 668:301-312 (1994)), Szepesy, L. et al. (J. Chromatog. 668:337-344 (1994)), Huddleston, J. G. et al. (Biotechnol. Bioeng. 44:626-635 (1994)), Watanabe, E. et al. (Annl. NY Acad. Sci. 721:348-364 (1994)), all of which are herein incorporated by reference.

A variety of commercially available HIC column chemistries which span a wide range of hydrophobicities should make it possible to find an appropriate ligand which allows for chromatographic separation. For example, HIC columns may be purchased from Synchrom and Bio-Rad (Hercules Calif.) covering the full range in available alkyl and aromatic ligands. In one embodiment, the HIC column used in the invention is methyl HIC.

Size Exclusion Chromatographic Material

In some embodiments, the chromatographic material comprises a size exclusion material wherein the size exclusion material is a resin or membrane. As intended herein, size-exclusion chromatography involves separating molecules primarily based on their size. The matrix used for size exclusion is preferably an inert gel medium which can be a composite of cross-linked polysaccharides, e.g., cross-linked agarose and/or dextran in the form of spherical beads. The degree of cross-linking determines the size of pores that are present in the swollen gel beads. Molecules greater than a certain size do not enter the gel beads and thus move through the chromatographic bed the fastest. Smaller molecules, such as detergent, protein, DNA and the like, which enter the gel beads to varying extent depending on their size and shape, are retarded in their passage through the bed. Molecules are thus generally eluted in the order of decreasing molecular size.

Porous chromatographic resins appropriate for size-exclusion chromatography of viruses may be made of dextran, and cross-linked dextrans. Most commonly used are those under the tradename, "SEPHADEX" available from Amersham Biosciences. The type of SEPHADEX, or other size-exclusion chromatographic resin used is a function of the type of VLP sought to be purified, and the nature of the cell culture lysate containing the VLP. Other size exclusion supports from different materials of construction are also appropriate, for example Toyopearl 55F (polymethacrylate, from Tosoh Bioscience, Montgomery Pa.) and Bio-Gel P-30 Fine (BioRad Laboratories, Hercules, Calif.).

For size exclusion chromatography a concentrated pool of partially purified VLPs are loaded onto a column containing an appropriate preparative size exclusion chromatography column (such as a column containing Sephadex G200 or Superpose 6 resins) that had been equilibrated in a suitable buffer (e.g., a phosphate buffer).

The present invention further provides chromatographic materials comprising an ion exchanger. The ion exchanger may be a cation exchanger wherein the cation exchanger comprises sulfate, phosphate and carboxylate derivitized chromatographic materials. The ion exchanger may also be an anion exchanger, wherein the anion exchanger comprises positively charged chromatographic material. The positively charged chromatographic material may be quaternary amine (Q) or diethylaminoethane (DEAE).

Anion Exchange Chromatographic Material

Anion Exchange chromatography uses a positively-charged organic moiety covalently cross-linked to an inert polymeric backbone. The latter is used as a support for the resin. Representative organic moieties are drawn from primary, secondary, tertiary and quaternary amino groups; such as trimethylaminoethyl (TMAE), diethylaminoethyl (DEAE), dimethylaminoethyl (DMAE), and other groups such as the polyethyleneimine (PEI) that already have, or will have, a formal positive charge within the pH range of approximately 5 to approximately 9.

In one embodiment, an anion exchange resin consisting of DMAE, TMAE, DEAE, or quaternary ammonium groups is used. A number of anion exchange resins sold under the tradename Fractogel (Novagen) use TMAE, DEAE, DMAE as the positively-charged moiety, and a methacrylate co-polymer background. Resins that use quaternary ammonium resins and quaternary ammonium resins of the type sold under the trade name Q SOURCE-30 (Amersham Biosciences) may also be employed. Q SOURCE-30 has a support made of polystyrene cross-linked with divinylbenzene.

Several possible anion exchange media are known that can be used in such columns including N-charged amino or imino resins such as POROS 50 PI™, Q SEPHAROSE™, any DEAE, TMAE, tertiary or quaternary amine, or PEI-based resin One skilled in the art will appreciate that recombinant VLPs can be purified on an anion exchange column either before or after purification on other columns.

The anion-exchange chromatographic resin, can be used in gravity column chromatography or high pressure liquid chromatography apparatus using radial or axial flow, fluidized bed columns, or in a slurry, that is, batch, method. In the latter method, the resin is separated from the sample by decanting or centrifugation or filtration or a combination of methods.

The principle of ion-exchange chromatography is that charged molecules adsorb to ion exchangers reversibly so that molecules can be bound or eluted by changing the ionic environment. Separation on ion exchangers is usually accomplished in two stages: first, the substance to be separated is bound to the exchanger, using conditions that give stable and tight binding; then the substance is eluted with buffers of different pH, or ionic strength, depending on the properties of the substance being purified.

More specifically, and as applied to the instant invention, the basic principle of ion-exchange chromatography is that the affinity of a VLP for the exchanger depends on both the electrical properties of the protein, and the relative affinity of other charged substances in the solvent. Hence, bound proteins can be eluted by changing the pH, thus altering the charge of the protein, or by adding competing materials, of which salts are but one example. Because different substances have different electrical properties, the conditions for release vary with each bound molecular species. In general, to get good separation, the methods of choice are either continuous ionic strength gradient elution or stepwise elution. For an anion exchanger, either pH is decreased and ionic strength is increased or ionic strength alone is increased. For a cation exchanger, both pH and ionic strength can be increased. The actual choice of the elution procedure is usually a result of trial and error and of considerations of stability of the VLPs being purified.

It will be appreciated by a skilled practitioner of this art, that the type of anion-exchanger, and the buffers, and salts used to bind and elute the VLP will also be a function of the type of VLP sought to be purified.

Cation Exchange Chromatographic Material

In cation exchange chromatography, a negative functional group is bound to the insoluble support medium. Accordingly, cation exchange chromatographic media bind positive counter ions when the incubation period is a sufficient time period to allow for the positively charged groups to bind to and come to equilibrium with the negatively charged cation exchanger medium. Neutral molecules and anions do not bind to the cation exchange medium. Following the electrostatic binding of species possessing a net positive charge, the cationic medium is washed, removing non-binding molecules from the medium. Bound ions are then eluted either by washing the medium with increasing concentrations of positive ions or by altering the pH of the medium. The disclosed invention contemplates using a variety of cation exchange media such as any sulfo-, phosphor carboxy-, or carboxy-methyl-based cation exchange resins bound to numerous support medium well known in the art.

In one embodiment of the invention, ion exchange chromatography may be used in binding mode or flow-through mode discussed below.

Affinity Chromatographic Material

In some embodiments, the chromatographic material comprises an affinity chromatographic material. The affinity chromatographic material may comprise antibodies, dye resins, and metals. The dry resin may be cibachrom blue or polymixin.

Affinity chromatography is a technique that provides for ligand specific purification of a target compound. As such, the technique exploits the structural and functional characteristic properties of macromolecules by binding the molecules based on these specific characteristics under certain conditions.

A variety of different affinity column matrices are contemplated for use with the disclosed invention. For example, antibodies directed against VLPs may be used to generate affinity column media that in turn can be used to purify VLPs. In addition, the affinity chromatographic material may comprise dry resins, and metals. The dry resin may be cibachrom blue or polymixin.

One embodiment of the disclosed invention contemplates the use of heparin as the adsorbent group. Affinity chromatography media containing heparin are commercially available from a variety of sources. For example, PerSeptive Biosystems, Inc. (Framingham, Mass.) markets a heparin-based medium (POROS 20HE™). When POROS 20HE™ is used as the affinity chromatography medium, the VLPs containing solution is applied to the affinity medium and subsequently eluted with an appropriate salt concentration.

The chromatographic materials discussed above can be run as individual steps, or sequentially, or in tandem. The sequence of the multistep chromatographic process of the present invention may be designed to produce VLPs meeting preset specifications. For example, the purification method of the present invention may be used to purify VLPs to greater than about 70%, 80, 90%, 95% or 99% purity.

In one embodiment, the sequence of the multistep chromatographic process is designed to control the resulting composition of VLPs. In another embodiment, the sequence of the multistep chromatographic process is designed to reduce contaminant levels to levels considered acceptable by regulatory agencies for pharmaceutical grade drug substance. For instance, the contaminant level of the host cell DNA content may be reduced to less than 1%. The contaminant level of the host cell protein content may be reduced to less than 5%. The sequence of the multistep chromatographic process is designed to make VLPs consistent with cGMP regulations and suitable for pharmaceutical testing in humans.

The present invention further provides a method of contacting a solution containing VLPs with a chromatographic material. In this regard, culture media or a cell lysate containing VLPs may be contacted with the chromatographic material wherein the culture media or cell lysate is filtered or purified by precipitation prior to contact with the chromatographic material. The solution or cell lysate may be centrifuged without a sucrose gradient. In one embodiment, a clarified solution containing VLPs is contacted with the chromatographic material. Alternatively, a VLP containing solution from one chromatographic step is contacted with another chromatographic material.

Certain embodiments of the disclosed invention contemplate the use of a hydroxyapatite medium in conjunction with a hydrophobic interaction chromatography medium to purify VLPs particles from the cellular milieu released during the lysis process. In one embodiment, the cell lysate is loaded on a hydroxyapatite column (Bio-Rad, CHT). Such columns are available commercially in a variety of sizes. Following purification over the hydroxyapatite column, the VLPs-containing material is passed over a hydrophobic interaction (HIC) column. The column is then washed and eluted. The purified sample of VLPs can be analyzed, for example, by silver-stained SDS-PAGE or size exclusion chromatography (SEC) for purity.

In one embodiment of the invention, a hydroxyapatite medium is used in conjunction with a hydrophobic interaction chromatographic medium and further in conjunction with a Anion exchange chromatographic medium in order to purify VLPs particles for pharmacological use. The present inventors have found that this combination is particularly suitable for purifying Norovirus Genotype I Norwalk viruses on a commercially scalable level. In addition, the present inventors have found that cation exchange chromatography followed by methyl HIC is particularly suitable for purifying Houston viruses.

Before contacting the chromatographic material with the VLP preparation in each step, it may be necessary to adjust parameters such as pH, ionic strength, and temperature and in some instances the addition of substances of different kinds. Adjustment of these parameters is within the knowledge of one skilled in the art and may be accomplished in the VLP containing solution or chromatographic medium. For example, the pH of the VLP containing solution may be adjusted with a buffer. The pH may be adjusted to either acidic values (e.g. pH less than 7) or basic values (e.g. pH greater than 7). In some embodiments, it may be desirable to adjust the pH of the solution or chromatographic material to a neutral value (e.g. pH equal to 7). The buffer used to adjust the pH value may comprise phosphate, carboxylate, sulfate, acetate, citrate, tris or his tris and the buffer concentration may be in the range of about 10 to 1000 mM.

In another embodiment, the method of the present invention involves adjustment of the ionic strength of the VLP containing solution. The ionic strength may be adjusted by the addition of a salt comprising cations and anions from the Hofmeister series. The salt may be a phosphate salt, such as sodium phosphate, calcium phosphate, and potassium phosphate. In some embodiments, the phosphate salt is sodium phosphate. The concentration of the salt may be in the range of about 10 to 500 mM. In one embodiment, the sodium phosphate concentration is about 100 mM.

Alternatively, an optional step may be performed on a chromatographic material by washing it with a solution (e.g., a buffer for adjusting pH, ionic strength, etc., or for the introduction of a detergent) to bring the necessary characteristics for purification of the VLP preparation. For example, the pH of the chromatographic material may be adjusted prior to VLP application by equilibration with a buffer. The pH may be adjusted to less than 7 or greater than or equal to 7 with a buffer comprising phosphate, carboxylate, or sulfate.

In another embodiment, the ionic strength of the chromatographic material may be adjusted by the addition of salt. The salt comprises cations and anions from the Hofmeister series such as ammonium sulfate. The concentration of ammonium sulfate may be greater than about 1, 2, or 2.4 molar.

In another embodiment, the ionic strength of the chromatographic material may be adjusted by the addition of a phosphate salt. In some embodiments, the phosphate salt is sodium phosphate. The sodium phosphate concentration may be in the range of about 10 to 500 mM. In one embodiment, the sodium phosphate concentration is about 100 mM. In yet another embodiment, the organic solvent concentration of the VLP containing solution can be adjusted during reversed phase processes.

Adjustment of the parameters of the VLP containing solution or chromatographic material can cause retention or pass-through of VLPs and contaminants. In one embodiment, the VLP containing solution or chromatographic material may be selected to cause retention of VLPs with contaminating materials passing through the chromatographic material. In another embodiment, the VLP containing solution or chromatographic material may be selected to cause retention of contaminating materials with VLPs passing through the chromatographic material. Such features can be utilized to operate the chromatographic steps in either "flow-through mode" or "binding mode" or a mixture thereof. The term "flow-through mode" refers to a VLP preparation separation technique in which at least one VLP contained in the preparation is intended to flow through a chromatographic resin or support, while at least one potential contaminant or impurity binds to the chromatographic resin or support. Flow-through mode may be used, for instance, in hydroxyapatite chromatography and ion exchange chromatography.

"Binding mode" refers to a VLP preparation separation technique in which at least one VLP contained in the preparation binds to a chromatographic resin or support, while at least one contaminant or impurity flows through. Binding mode may be used, for instance, in hydroxyapatite chromatography and ion exchange chromatography.

In certain embodiments, the present invention provides methods for removing contaminating materials from VLP preparations using hydroxyapatite chromatography or hydrophobic interaction chromatography in binding mode, flow-through mode, or a combination thereof. Such practice has application to the large scale purification of VLP preparations.

In binding mode hydroxyapatite chromatography, the method uses a hydroxyapatite support charged with phosphate at neutral pH and low ionic strength to bind VLPs. The column is then washed with a phosphate buffer to remove loosely bound impurities. Next, the VLPs are selectively eluted using a high ionic strength phosphate buffer containing 100 to 200 mM phosphate. Lastly, the resin is optionally regenerated using a sodium hydroxide and potassium phosphate solution.

In flow-through mode hydroxyapatite chromatography, a VLP preparation is buffer-exchanged into a load buffer at an appropriate pH. The VLP preparation is then allowed to flow through a hydroxyapatite column, while impurities bind to the column. The column is optionally subsequently washed and cleaned to allow additional VLPs to flow through the column and be purified. Lastly, the column may optionally be stripped and then regenerated using buffer such as a sodium hydroxide and potassium phosphate solution.

In combination binding/flow-through mode hydroxyapatite chromatography, the hydroxyapatite media is equilibrated and washed with a solution, thereby bringing the necessary characteristics for purification of the VLP preparation.

Prior to equilibration and chromatography, the hydroxyapatite chromatography medium may be pre-equilibrated in a chosen solution, e.g. a salt and/or buffer solution. Pre-equilibration serves the function of displacing a solution used for regenerating and/or storing the chromatography medium. One of skill in the art will realize that the composition of the pre-equilibration solution depends on the composition of the storage solution and the solution to be used for the subsequent chromatography. Thus, appropriate pre-equilibration solutions may include the same buffer or salt used for performing the chromatography, optionally, at a higher concentration than is used to perform chromatography.

Before the sample is applied to the column, the hydroxyapatite chromatography medium can be equilibrated in the buffer or salt that will be used to chromatograph the VLP. Chromatography (and loading of the protein to be purified) can occur in a variety of buffers or salts including sodium, potassium, ammonium, magnesium, calcium, chloride, fluoride, acetate, phosphate, and/or citrate salts and/or Tris buffer. Such buffers or salts can have a pH in a range from about 2 to about 10. In some embodiments, equilibration may take place in a solution comprising a Tris or a sodium phosphate buffer. Optionally, the sodium phosphate buffer is at a concentration between about 0.5 millimolar and about 50 millimolar, more preferably at a concentration between about 15 millimolar and 35 millimolar. Preferably, equilibration takes place at a pH of at least about 5.5. Equilibration may take place at pHs between about 6.0 and about 8.6, preferably at pHs between about 6.5 and 7.5. Most preferably, the solution comprises a sodium phosphate buffer at a concentration of about 25 millimolar and at a pH of about 6.8.

The contacting of a VLP preparation to the hydroxyapatite resin in either binding mode, flow-through mode, or combinations thereof may be performed in a packed bed column, a fluidized/expanded bed column containing the solid phase matrix, and/or in a simple batch operation where the solid phase matrix is mixed with the solution for a certain time.

After contacting the hydroxyapatite resin with the VLP preparation there is optionally performed a washing procedure. However, in some cases, the washing procedure may be omitted, saving a process-step as well as washing solution. The washing buffers employed will depend on the nature of the hydroxyapatite resin, the mode of hydroxyapatite chromatography being employed, and therefore can be determined by one of ordinary skill in the art. In flow-through mode and combination binding/flow-through mode, the purified VLP flow-through obtained after an optional wash of the column may be pooled with other purified VLP fractions.

In binding mode, the VLP may be eluted from the column after an optional washing procedure. For elution of the VLP from the column, this invention uses a high ionic strength phosphate buffer. For example, the elution buffer may contain 1 to 300 mM sodium phosphate, in another embodiment it may contain 50 to 250 mM sodium phosphate, in another embodiment it may contain 100 to 200 mM sodium phosphate, in another embodiment may contain 150 mM sodium phosphate. The pH of the elution buffer may range from 6.4 to 7.6. In one embodiment, the pH may be from 6.5 to 7.3, in another embodiment the pH may be 7.2, and in another embodiment the pH may be 6.8. The elution buffer may be altered for elution of the VLP from the column in a continuous or stepwise gradient. Buffer components may be adjusted according to the knowledge of the person of ordinary skill in the art.

In both binding, flow-through mode, and combinations thereof, a solid phase matrix may optionally be cleaned, i.e. stripped and regenerated, after elution or flow through of the VLP. This procedure is typically performed regularly to minimize the building up of impurities on the surface of the solid phase and/or to sterilize the matrix to avoid contamination of the product with microorganisms.

In certain embodiments, the hydroxyapatite chromatography step is conducted first, the hydrophobic interaction chromatography step is conducted second, and either anion exchange or size exclusion chromatography step is conducted third.

VLPs are generally recovered from an hydroxyapatite step in the fractions of binding, flow-through or a mixture thereof. The salt concentration and pH of such fractions can then be adjusted for purification over a hydrophobic interaction column or for purification over any other suitable affinity column, as described in Example 1. In accordance with this method, ammonium sulfate is added to a final concentration of 8% w/v to pooled VLPs and the sample is stirred until all of the ammonium sulfate is dissolved. A column containing 250 mL of HIC resin is equilibrated with five CV of 100 mM sodium phosphate, 2.4 M ammonium sulfate pH 6.8 and the VLP suspension loaded. The column is washed with approximately three CV of buffer C until a stable baseline is observed and then washed with 10 CV of 70% 100 mM phosphate, pH 6.8. The VLPs can be eluted from the column with 150 mM phosphate.

It should be noted that the order of the chromatographic media is not considered to be important to the ultimate purification of the VLPs particles. Also, a size exclusion column may optionally be used to further purify the sample. The yields obtained using such combinations are predictable based on the yields obtained using the individual column-purification steps.

VLPs eluted from HIC column can be subjected to additional size exclusion purification steps as required. In one embodiment of the invention, eluate purified by combination hydroxyapatite chromatography and HIC chromatography was further purified by a DEAE anion exchange chromatography.

Any or all chromatographic steps of the invention can be carried out by any mechanical means. Chromatography may be carried out in a column. The column may be run with or without pressure and from top to bottom or bottom to top. The direction of the flow of fluid in the column may be reversed during the chromatography process. Chromatography may also be carried out using a batch process in which the solid support is separated from the liquid used to load, wash, and elute the sample by any suitable means, including gravity, centrifugation, or filtration. Chromatography may also be carried out by contacting the sample with a filter that adsorbs or retains some molecules in the sample more strongly than others.

Finally, the eluate from the Anion exchange column may be filtrated through a diafilter or a tangential flow filter to concentrate the filtrate.

Additional Optional Steps

Although it has been discovered that hydroxyapatite and hydrophobic interaction chromatography can be used together to separate VLP, as mentioned above, the purification method of the invention can be used in combination with other protein purification techniques. In one embodiment of the invention, one or more steps preceding the hydroxyapatite step may be desirable to reduce the load challenge of the contaminants or impurities. In another embodiment of the invention, one or more purification steps following the hydrophobic interaction step may be desirable to remove additional contaminants or impurities.

The hydroxyapatite purification procedure described may optionally be combined with other purification steps, including but not limited to, Protein A chromatography, affinity chromatography, hydrophobic interaction chromatography, immobilized metal affinity chromatography, size exclusion chromatography, diafiltration, ultrafiltration, viral removal filtration, and/or ion exchange chromatography.

Further purification methods may include filtration, precipitation, evaporation, distillation, drying, gas absorption, solvent extraction, press extraction, adsorption, crystallization, and centrifugation. Other purification methods may include further chromatography according to this invention utilizing batch or column chromatography. In addition, further purification can include combinations of any of the forgoing, such as for example, combinations of different methods of chromatography, combinations of chromatography with filtration, combinations of chromatography with precipitation, or combinations of membrane treatment with drying.

Elution of VLPs can be monitored by techniques known in the art including optical density, transmission electron microscopy, or light scattering. Additionally, the biological properties of the VLPs prior to and after purification can be determined using well established assays. More specifically, the VLP purity and identity may be measured using a variety of analytical methods including, reduced and non-reducing sodium dodecyl sulfate polyacrylamide gel electrophoresis (SDS-PAGE), size exclusion chromatography, HPLC (high performance liquid chromatography), capillary electrophoresis, MALDI (Matrix Assisted Laser Desorption Ionization) mass spectrometry, ELISA (Enzyme Linked Immunosorbent Assay), or circular dichroism.

The following examples are included to demonstrate preferred embodiments of the invention. A skilled practitioner of the art would, in light of the present disclosure, appreciate that many changes can be made in the specific embodiments and obtain a similar result without departing from the spirit and scope of the invention.

Example 1. Purification of Norovirus Genogroup I Viruses

General Description of Method

The purification process consists of 3 chromatography steps. The steps use orthogonal mechanisms resulting in a scalable process that produces highly purified VLPs. The first step of the purification is a capture step that uses Bio-Rad hydroxyapatite (CHT) resin. The CHT step concentrates Norwalk VLPs, eliminates media components, and exchanges the product to a phosphate buffer. Following the addition of ammonium sulfate, methyl hydrophobic interaction chromatography (HIC) provides the majority of the purification as shown in FIG. 1. The third chromatographic step is a DEAE ion exchange chromatography operated in in-flow mode. Under the conditions used, Nowalk VLPs do not bind to the column and residual contaminants (endotoxin, nucleic acid, and proteins) are retained. The final step in the purification process is an ultra filtration where phosphate buffer is replaced by water for injection. Bulk drug substance (Norwalk VLPs) is stored as a 0.5 to 1.5 mg/mL suspension at 2-8° C.

A number of tests on the chromatographically-purified VLPs can be conducted to determine whether there is any difference between the chromatographically-purified VLPs and ultracentrifuge-purified VLPs. These methods include transmission electron microscopy and physical/chemical characterization, including melting points by circular dichroism spectra, dynamic light scattering, size exclusion chromatography and high performance liquid chromatography. The chromatography purification procedures are outlined below. The purification process can be normalized for any scale. Linear flow rates listed are independent of column diameter.

Purification of VLPs

A 15 L fermentation produces 10 L of conditioned media. The purification process described below is designed to handle 5 L. To purify the entire 10 L, 2 campaigns using 5 L each are performed over a two week period.

Figure 2:
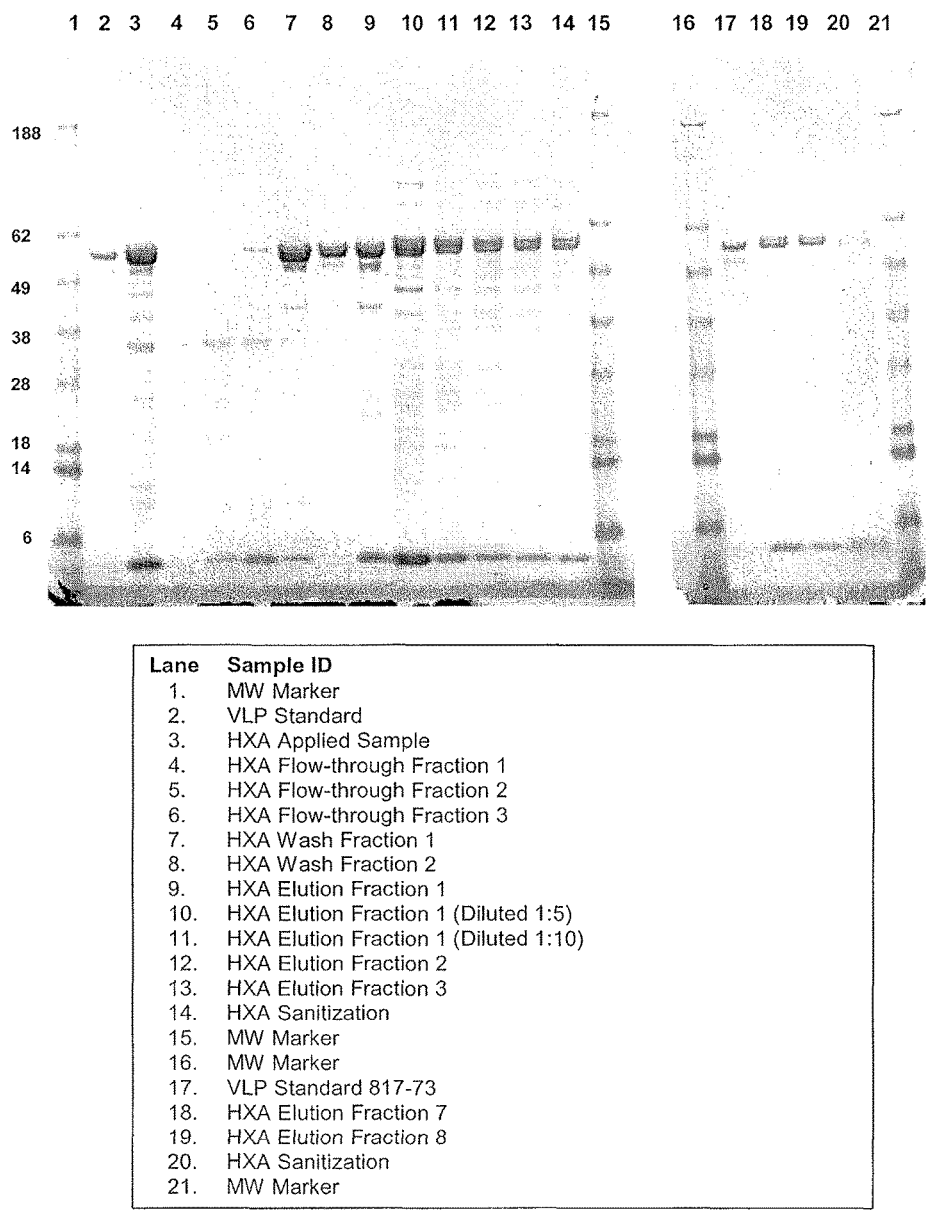
FIG. 2 is a SDS-PAGE gel/Coomassie Stain of Hydroxyapatite Chromatography Column Fractions.

HA Column Chromatography:

Five liters of culture supernatant is loaded onto a column packed with 500 mL of hydroxyapatite (Bio-Rad, CHT) resin, equilibrated by passing 10 column volumes of 5 mM sodium phosphate buffer (buffer A) with a flow rate of 80 mL/min. The culture supernatant, is loaded onto the column and washed with two column volumes (CV) of buffer A. 150 mM phosphate (buffer B) is used to elute the Norwalk VLPs from the CHT column. The Norwalk VLPs elute as a single peak off in buffer B. Fractions (1 CV each) are collected during the chromatographic run and analyzed by SDS-PAGE. The fractions containing VLPs are pooled for the next step in the purification. SDS-PAGE with Coomassie Stain of Hydroxyapatite chromatography fractions are shown in FIG. 2. The majority of the Norwalk VLPs elute in the 4 eluate column volume fractions with the 100% buffer B. These pooled fractions were used for the hydrophobic interaction chromatography (HIC) purification step 2

Figure 3:
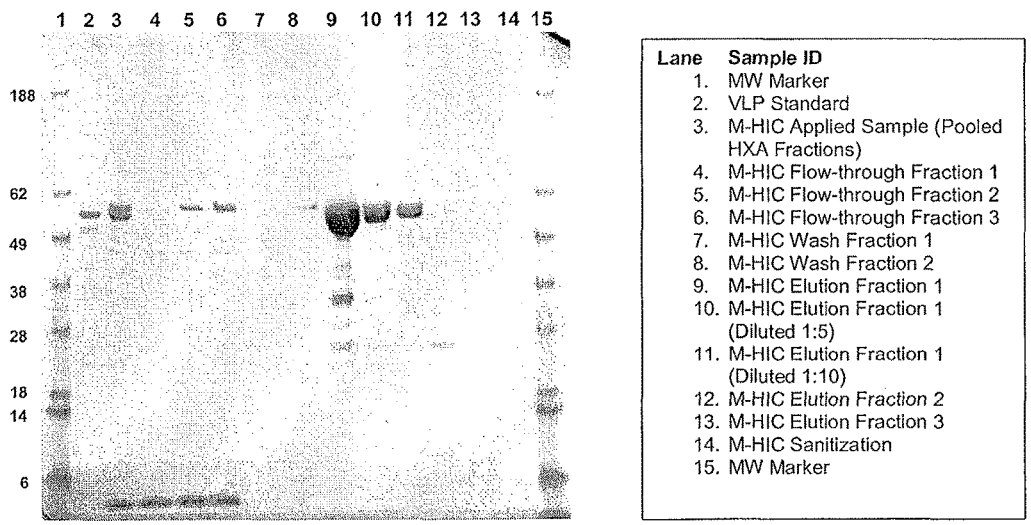
FIG. 3 is a SDS-PAGE gel/Coomassie Stain of HIC Chromatography Column Fractions.

HIC Column Chromatography:

To the pooled VLP fractions from the CHT chromatography step, solid ammonium sulfate is added to a final concentration of 8% w/v and the sample stirred until all of the ammonium sulfate is dissolved. Addition of ammonium sulfate facilitates absorption of the protein onto BioRad Methyl HIC resin. A column containing 250 mL of HIC resin is equilibrated with five CV of 100 mM sodium phosphate, 2.4 M ammonium sulfate pH 6.8 (buffer C) and the VLP suspension loaded. The column is washed with approximately three CV of buffer C until a stable baseline is observed and then washed with 10 CV of 70% 100 mM phosphate, pH 6.8 (buffer D). VLPs from the HIC Column elute in three to four CV of 100% buffer B. During elution 250 mL (1 CV) fractions are collected and analyzed by SDS-PAGE. Fractions containing VLPs are pooled and used in the DEAE chromatographic step. SDS-PAGE/Coomassie stain of HIC column fractions are shown in FIG. 3.

Figure 4:
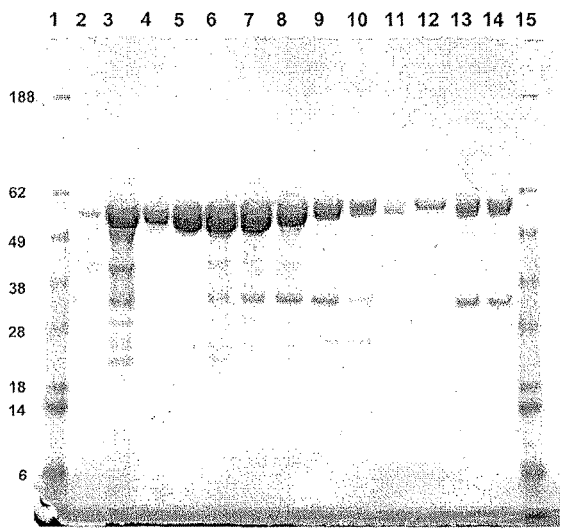
FIG. 4 is a SDS-PAGE gel/Coomassie Stain of DEAE Chromatography Column Fractions.

DEAE Column Chromatography:

Pooled fractions, containing the partially purified VLPs from the methyl HIC column, are loaded directly onto a column packed with 270 mL DEAE Sephadex resin. Phosphate buffer pH 6.5 is pumped at a flow rate of 40 mL/min causing the VLPs to elute in the void volume (flow through). Contaminating proteins interact with the resin and elute later in the chromatography. Fractions (¼ CV each) are collected upon sample loading and as soon as UV detector signal rises above baseline. Fractions are analyzed by SDS-PAGE and fractions containing VLPs pooled for buffer exchange by Diafiltration. SDS-PAGE/Coomassie stain of DEAE column fractions are shown in FIG. 4.

Figure 5:
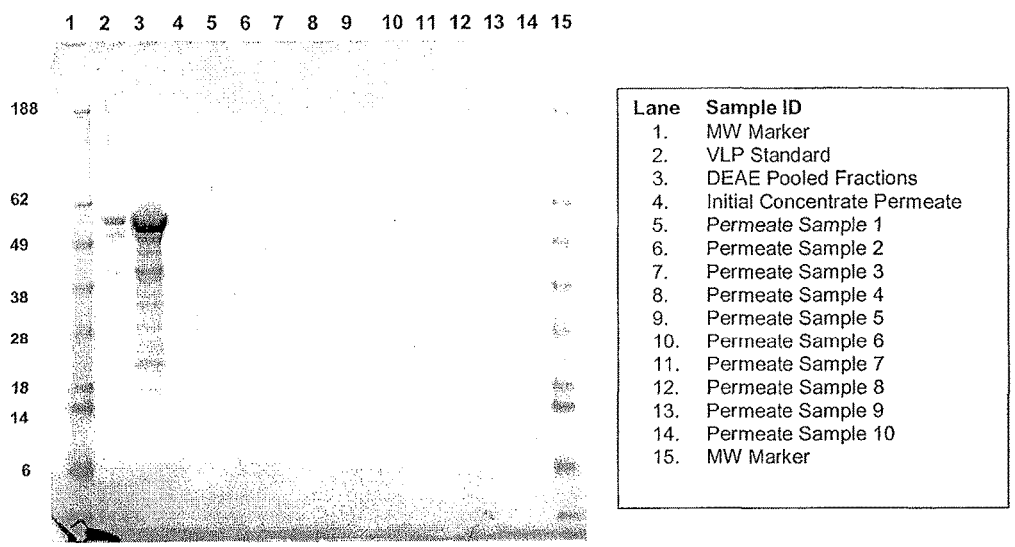
FIG. 5 is a SDS-PAGE gel/Coomassie Stain of Diafiltraion Fractions.
Figure 6:
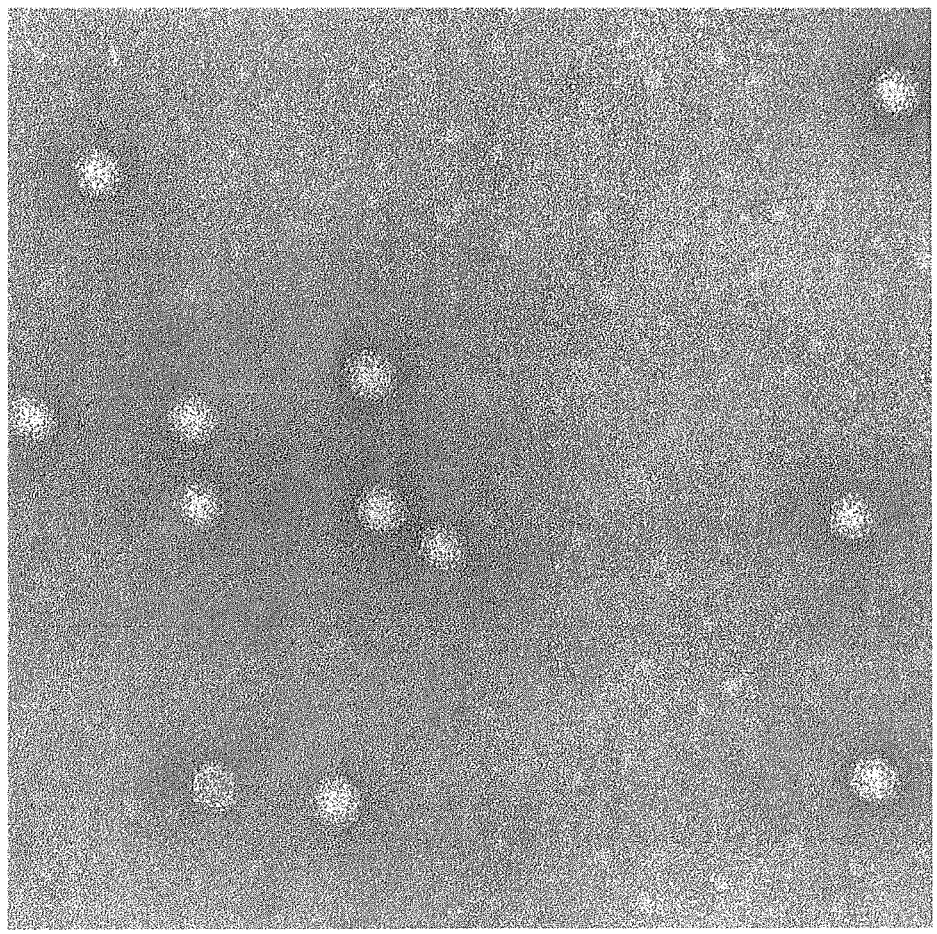
FIG. 6 is an image of transmission Electron Micrograph of Norwalk virus VLPs purified chromatographically. Particles are approximately 34 to 38 nM range in size.
Figure 7:
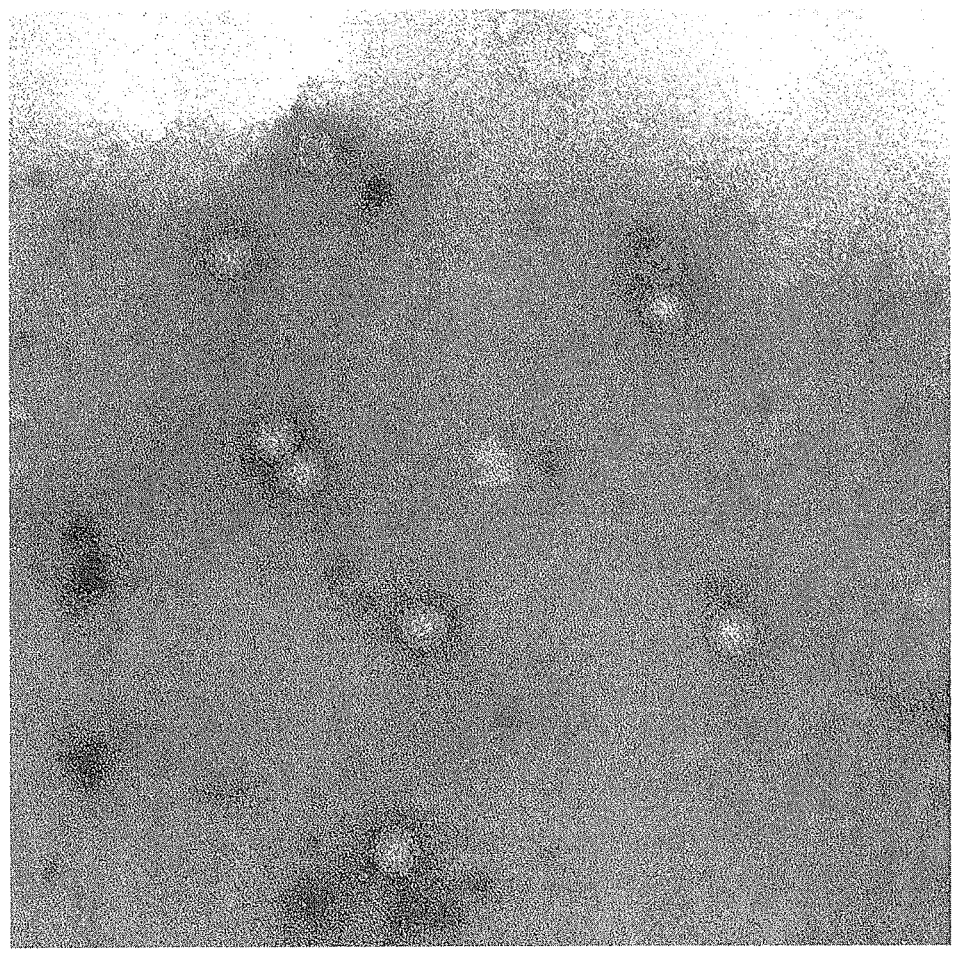
FIG. 7 is an image of transmission Electron Micrograph of Norwalk virus VLPs purified by ultracentrifugation. These particles are also 34 to 38 nM in size.
Figure 8:
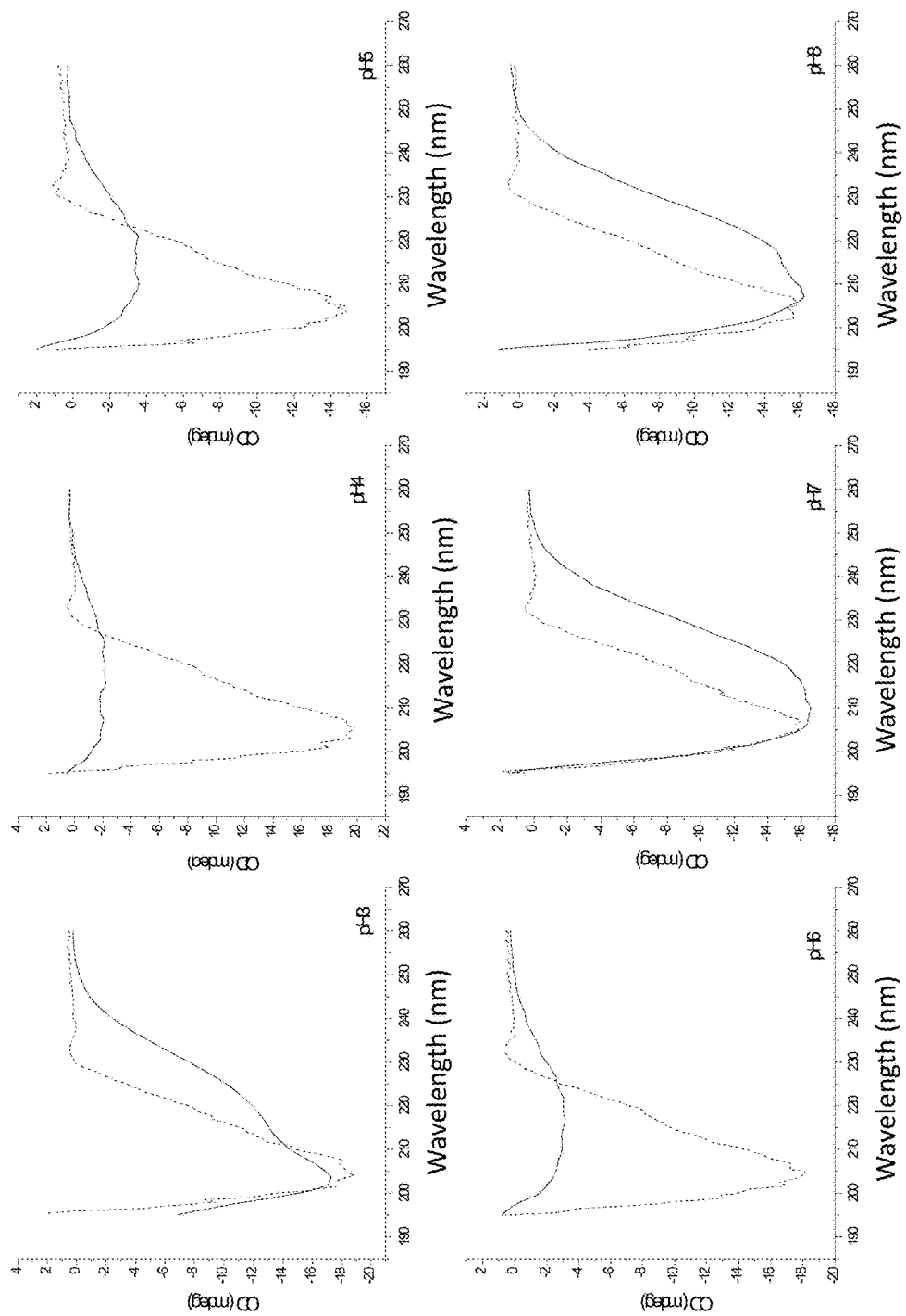
FIG. 8 is a graph showing CD spectra of column-purified VLPs at 10° C. (dash line) and 90° C. (solid line) as a function of pH.
Figure 9:
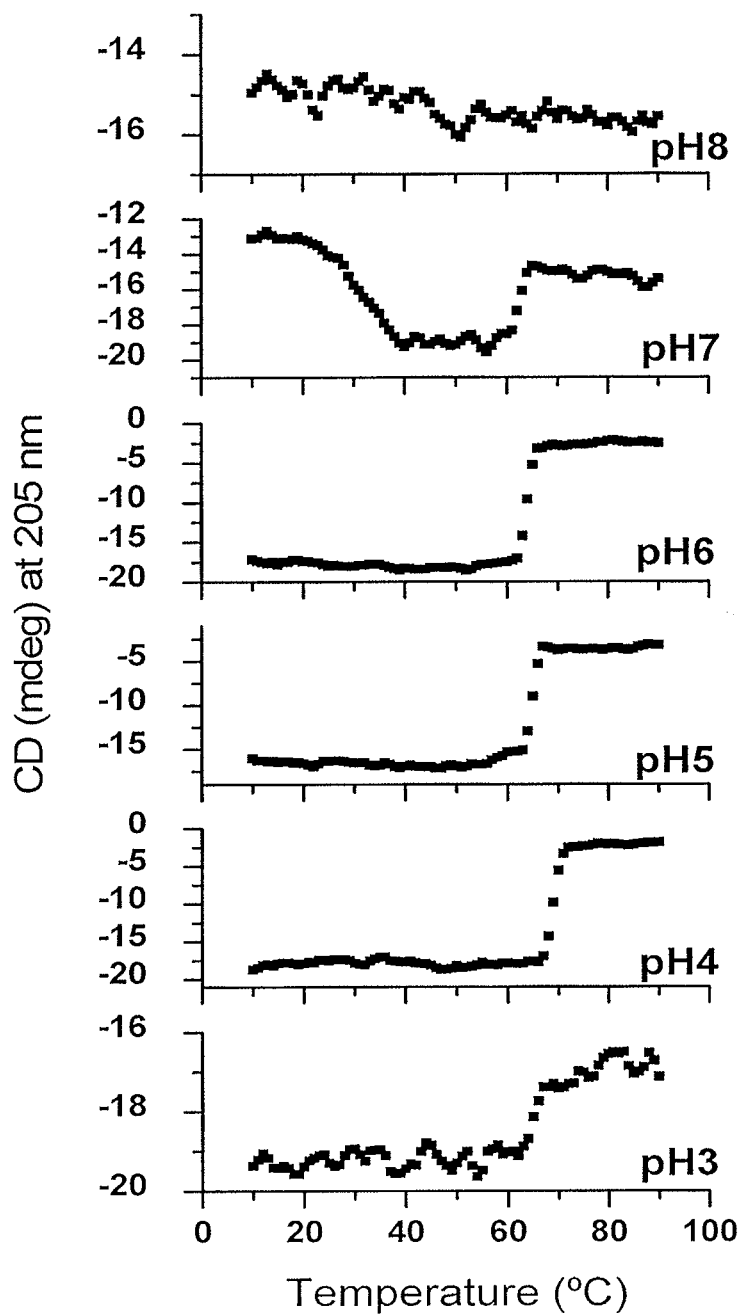
FIG. 9 is a graph showing CD signal of column-purified VLPs monitored at 205 nm as a function of temperature and pH.
Figure 10:
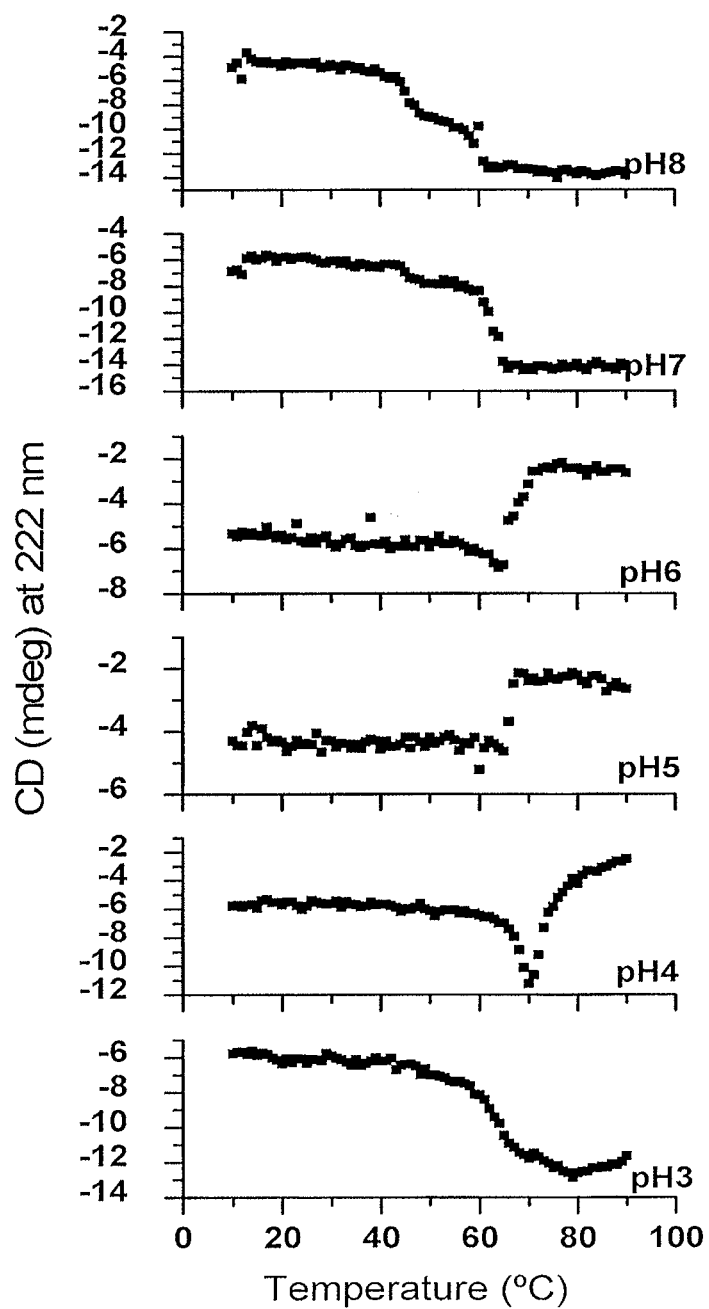
FIG. 10 is a graph showing CD signal of column-purified VLPs monitored at 222 nm as a function of temperature and pH.
Figure 11:
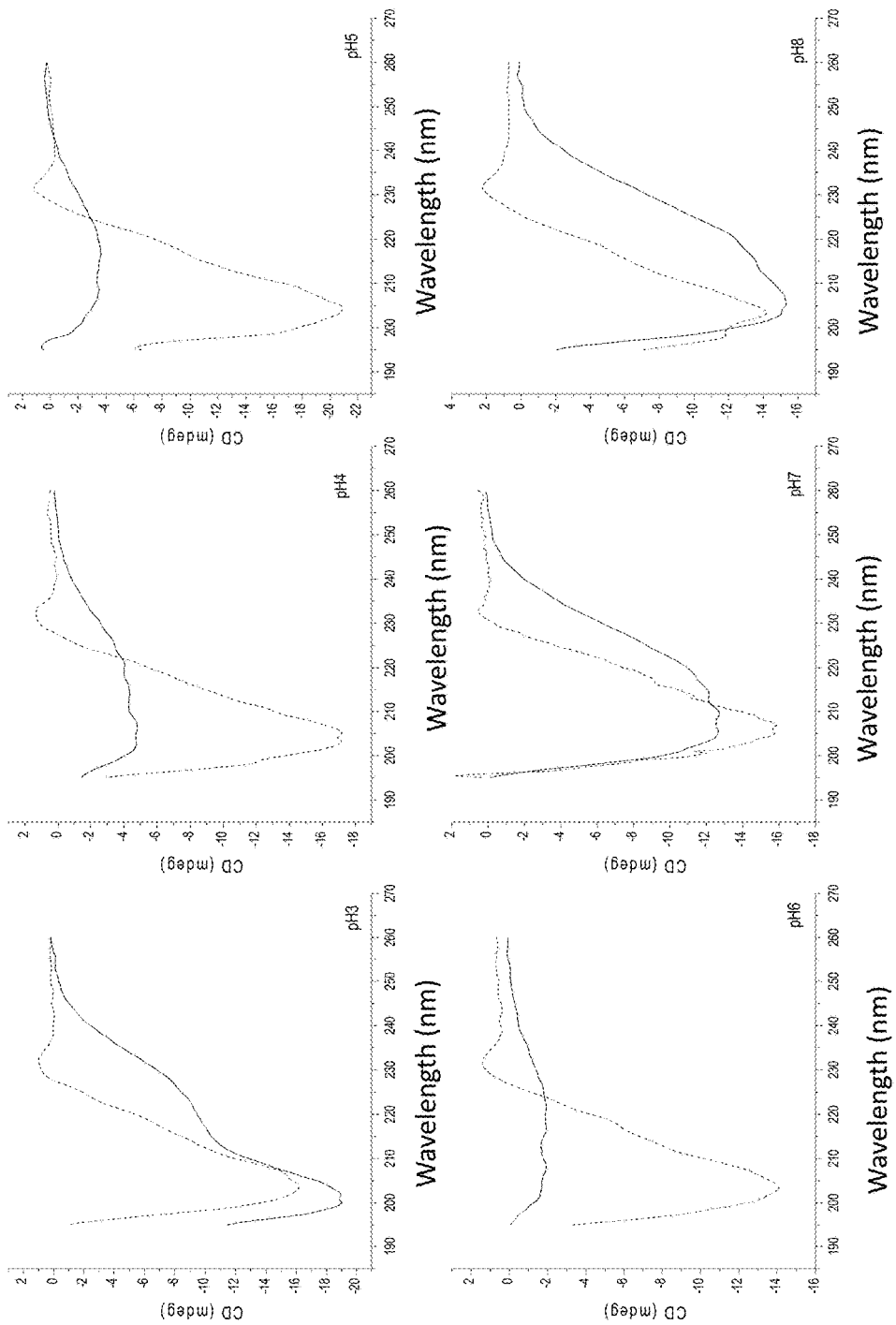
FIG. 11 is a graph showing CD spectra at 10° C. (dash line) and 90° C. (solid line) as a function of pH, of VLPs purified by ultracentrifugation.
Figure 12:
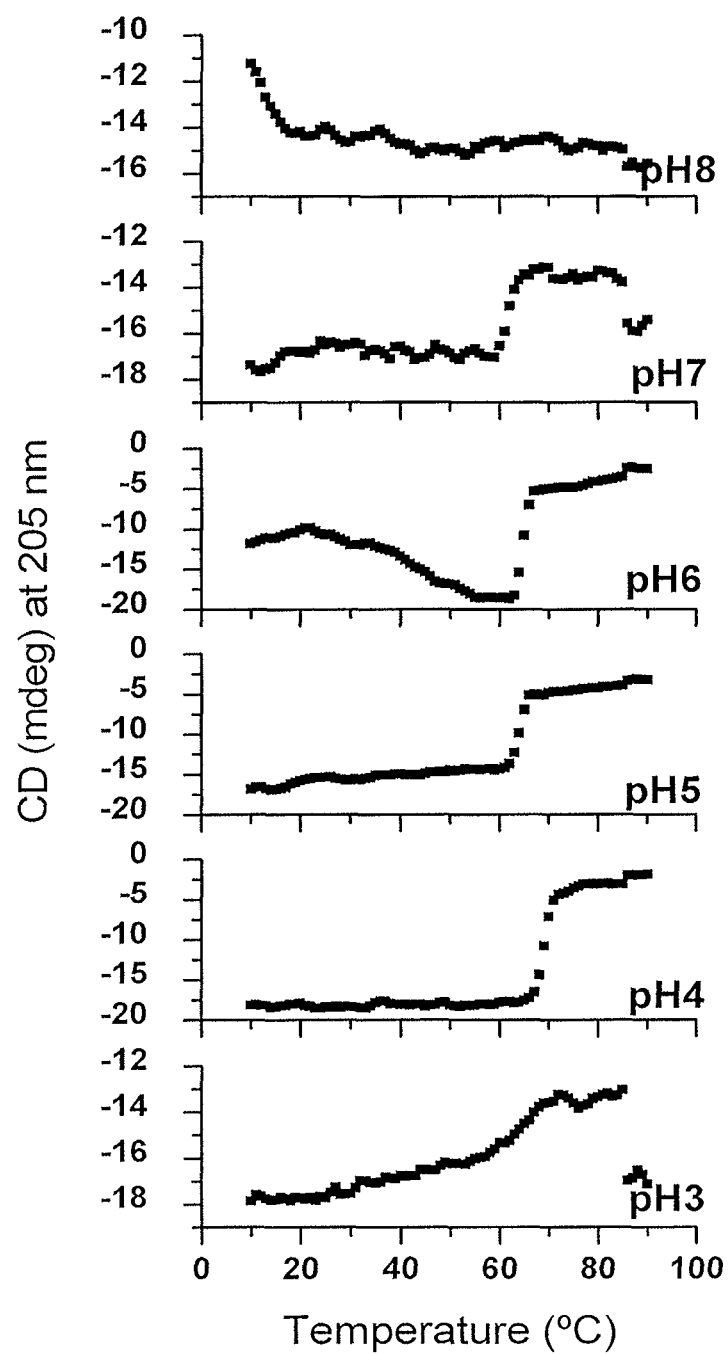
FIG. 12 is a graph showing CD spectra at 205 nm as a function of temperature and pH of VLPs purified by ultracentrifugation.
Figure 13:
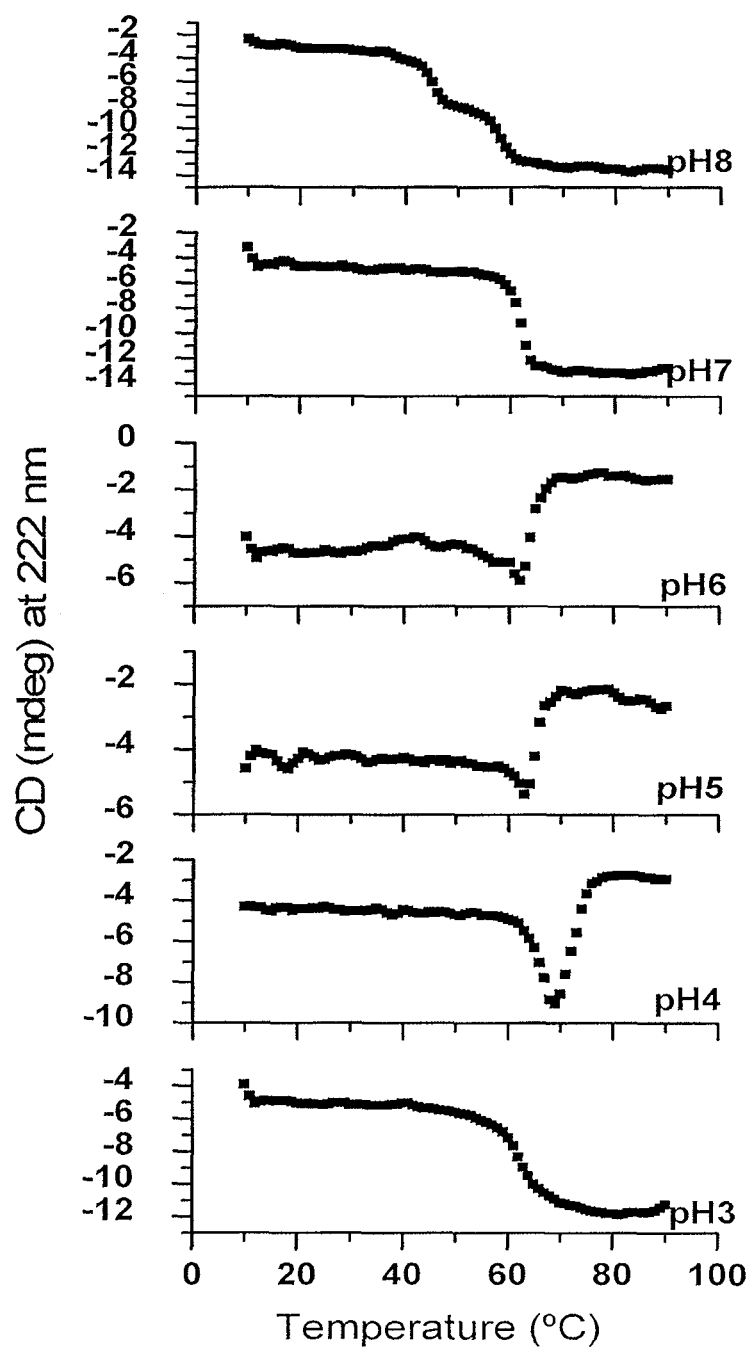
FIG. 13 is a graph showing CD signal at 222 nm as a function of temperature and pH, of VLPs purified by ultracentrifugation.

Diafiltration:

In the final purification step Norwalk VLPs, which elute from the DEAE column are diafiltered and concentrated. This procedure involves placing the VLPs in a sanitized stirred cell diafiltration apparatus. The volume of liquid is reduced by 50% and water for injection is added back to the original volume. This process was repeated a total of 10 times. The retentate contains the diafiltered Norwalk VLPs. This material then goes through a final sterile filtration process. Aliquots are taken for QC testing and release. SDS-PAGE/Coomassie stain from diafiltration fractions are shown in FIG. 5.

VLP Content:

Throughout purification, coomassie stained SDS-PAGE gels are used to identify fractions containing VLPs. During purification, a fraction is assumed to contain VLPs if a band is observed that migrates with a similar molecular weight as a VLP reference material run on the same gel. Only those fractions where the VLP band has an intensity equivalent to or greater than the intensity of VLP standard are pooled.

Protein Concentration:

In-process protein concentration (ultra filtration step) is determined by chromogenic assay based on bicinchonic acid reaction with protein. Test reagents are obtained from Pierce.

The specifications of the Norwalk virus VLPs purified chromatographically by the method described above are shown in Table 1. The chromatographically purified Norwalk virus VLPs were also compared to the VLPs purified by the ultracentrifugation method using transmission electron microscopy (TEM) and CD spectra. The results are shown in FIGS. 6-13.

TABLE 1

| Test | Specification | Result |
|---|---|---|
| Identify | Confirmed for | |
| | a. Molecular weight by SDS-PAGE protein band between 49 and 62 KDa | Complies |
| | b. 49 to 62 kDa protein detected by Western blot | Complies |
| Protein Concentration | 0.5 mg/mL to 1.5 mg/mL | 1.40 mg/mL |

TABLE 1-continued

| Test | Specification | Result |
|---|---|---|
| Purity | Greater than 90% size exclusion chromatography | >99% |
| Host Cell DNA | <100 pg/mL | <100 pg/mL |
| Baculovirus DNA | <100 pg/mL | >31 & <62 pg/mL |
| Host Cell Protein | Not more than 5% | <0.3% |
| Endotoxin | Less than 640 EU/mL | >320 & <640 EU/mL |
| pH | ≤7.0 | 5.4 |

Example 2. Purification of Norovirus Genogroup II Viruses

General Description of Method

The Houston purification process also utilizes orthogonal mechanisms resulting in a scalable process that produces highly purified VLPs. In constrast to the Norwalk purification process that utilizes HA, HIC and Anion Exchange, we find that a 2 column process works well for genogroup 11.4 Houston virus VLPs.

To purify Houston VLPs, conditioned media containing VLPs is clarified by either filtration or centrifugation and loaded on to a cation exchange SP FF resin equilibrated with 20 mM citrate phosphate buffer, pH 4.0. Following a wash with 20% elution buffer (20 mM citrate phosphate, 1M sodium chloride), the VLPs are eluted using step gradient and 100% elution buffer.

The fractions from the cation exchange column which contain Houston VLPs are pooled and the ionic strength adjusted through the addition of 15% (w/v) ammonium sulfate. This pooled material is then loaded onto a column containing methyl HIC resin with phosphate buffer at pH 6.8 containing 2.4 M ammonium sulfate (buffer A). After loading, a 3 step gradient elution is used to elute the VLPs from the HIC resin. In the first step, 40% elution buffer (100 mM sodium phosphate) is used to elute contaminants. Next, the gradient is stepped up to 70% elution buffer which causes the VLPs to elute and finally the gradient is adjusted to 100% elution buffer to ensure that elution is complete and to elute any remaining contaminants. The elution peak containing VLPs from methyl HIC chromatography in 70% elution buffer is then dialyzed into 20 mM citrate phosphate buffer and 150 mM sodium chloride to pH 6.0.

Based on small-scale production runs, the process results in 5 to 15 mg of purified VLPs from 200 and 500 mL spinner flasks and results in a VLP purity of greater than 90% by SDS-PAGE.

Figure 14:
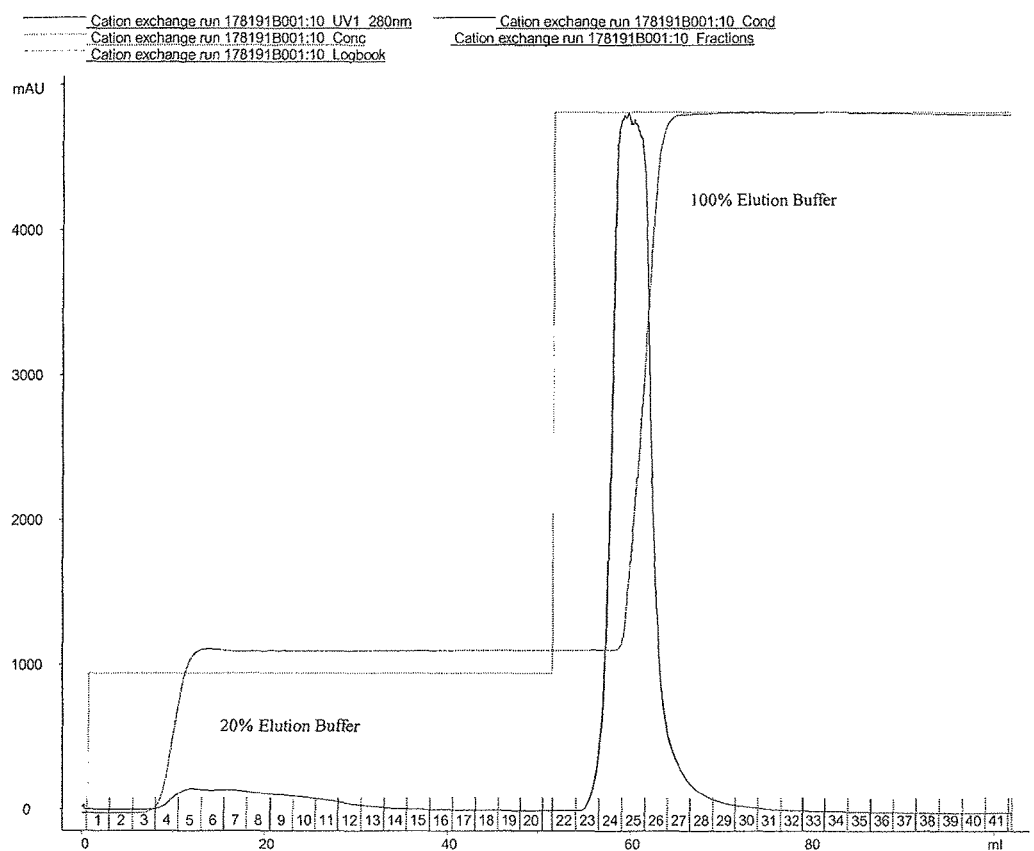
FIG. 14 is a chromatogram from the Cation Exchange purification step used for Houston virus VLPs.
Figure 15:
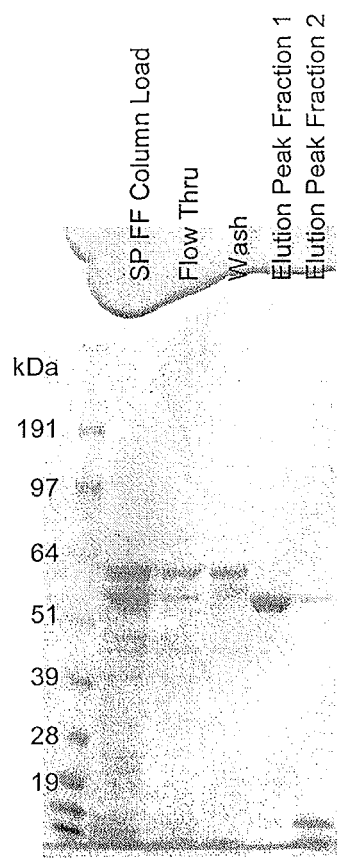
FIG. 15 is a SDS-PAGE gel/Coomassie Stain of Cation Exchange fractions of Houston virus VLPs.
Figure 16:
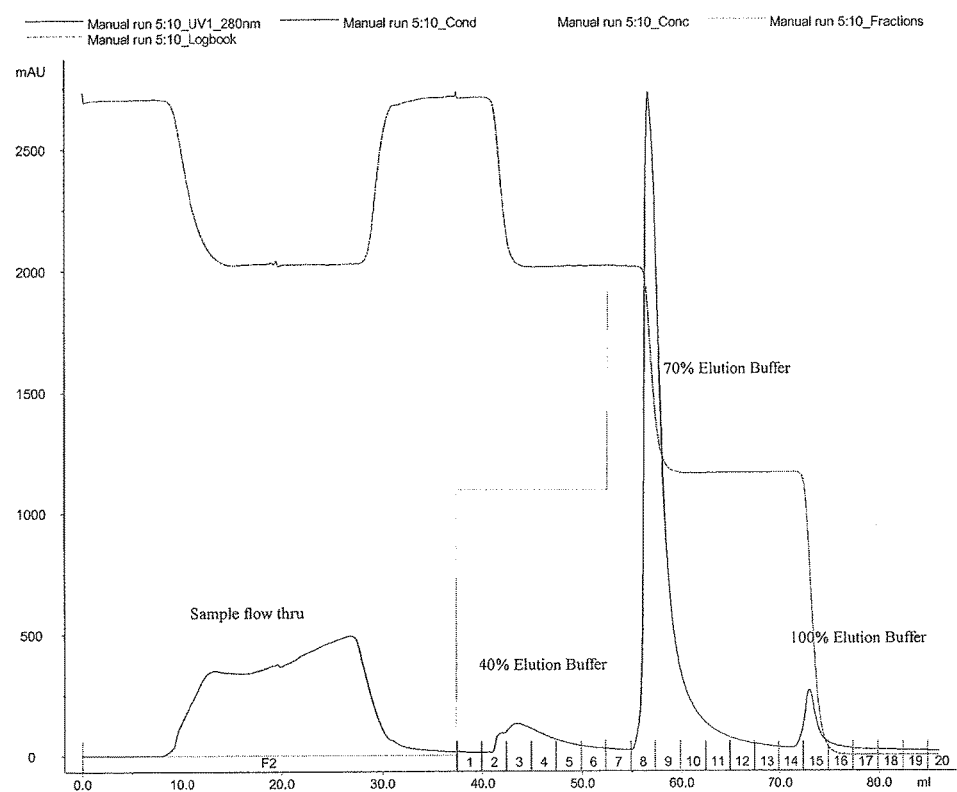
FIG. 16 is a chromatogram from Methyl HIC Chromatography purification step used for Houston virus VLPs.
Figure 17:
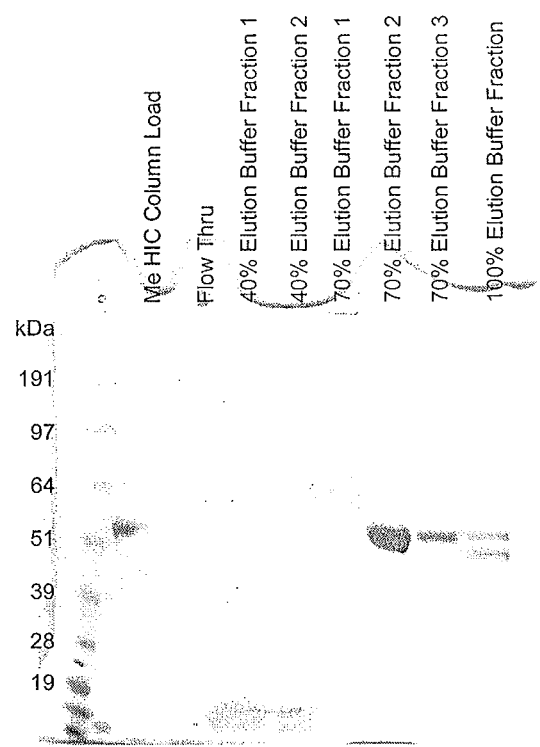
FIG. 17 is a SDS-PAGE gel/Coomassie Stain of Methyl HIC fractions of Houston virus VLPs.
Figure 18:
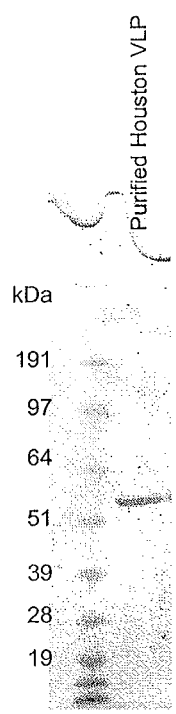
FIG. 18 is a SDS-PAGE gel/Coomassie Stain of purified Houston virus protein.
Figure 19:
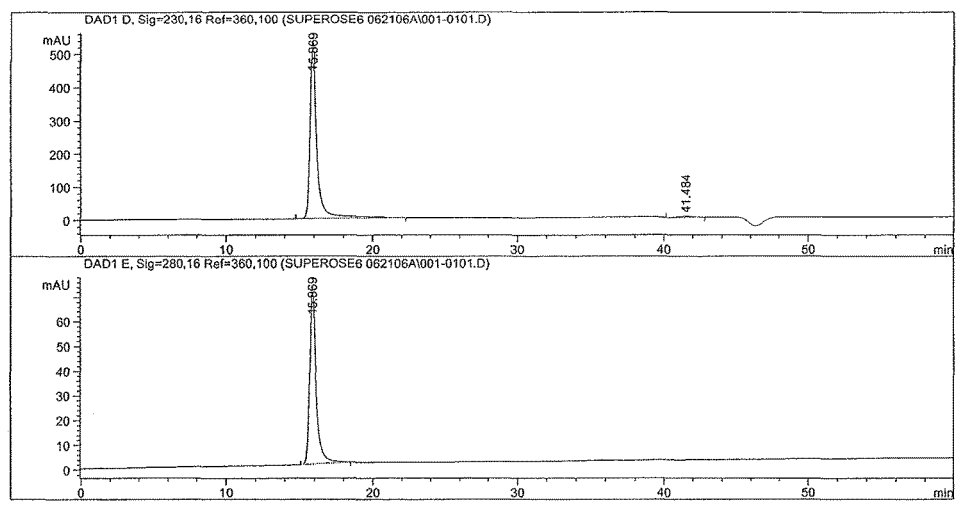
FIG. 19 is an HPLC-SEC chromatogram of purified Houston virus protein.
Figure 20:
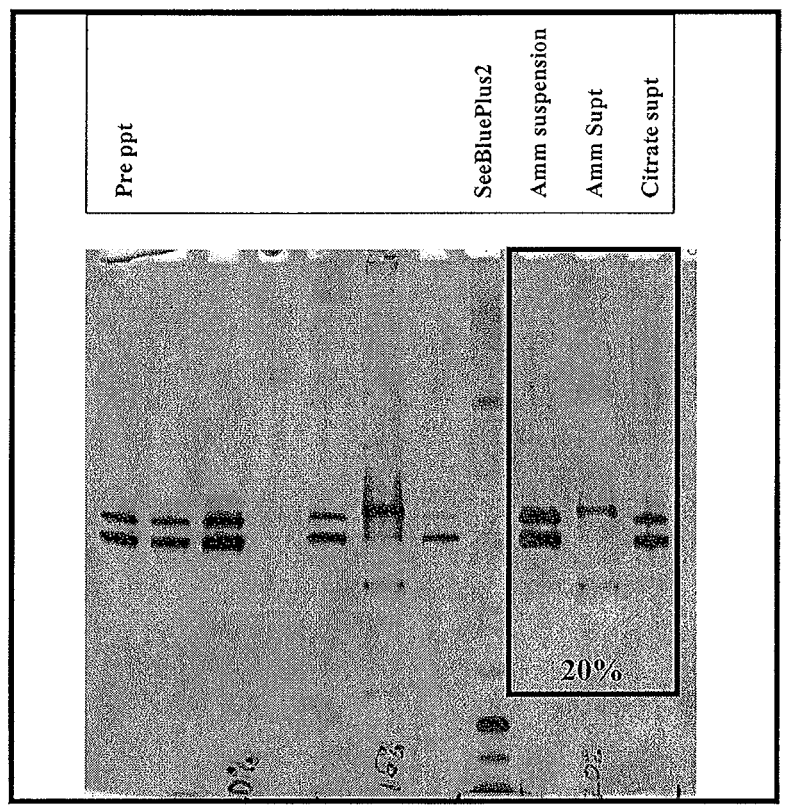
FIG. 20. Silver stained SDS-PAGE gel showing purification of a Houston VLP preparation with a 20% ammonium sulfate precipitation. "Amm suspension" is the initial ammonium sulfate suspension. "Amm Supt" is the supernatant which results when the ammonium sulfate suspension is centrifuged. "Citrate supt" is the dissolved precipitated material. Of interest is the "amm supt" lane which highlights the amount of non-precipitated contaminant material.
Figure 21:
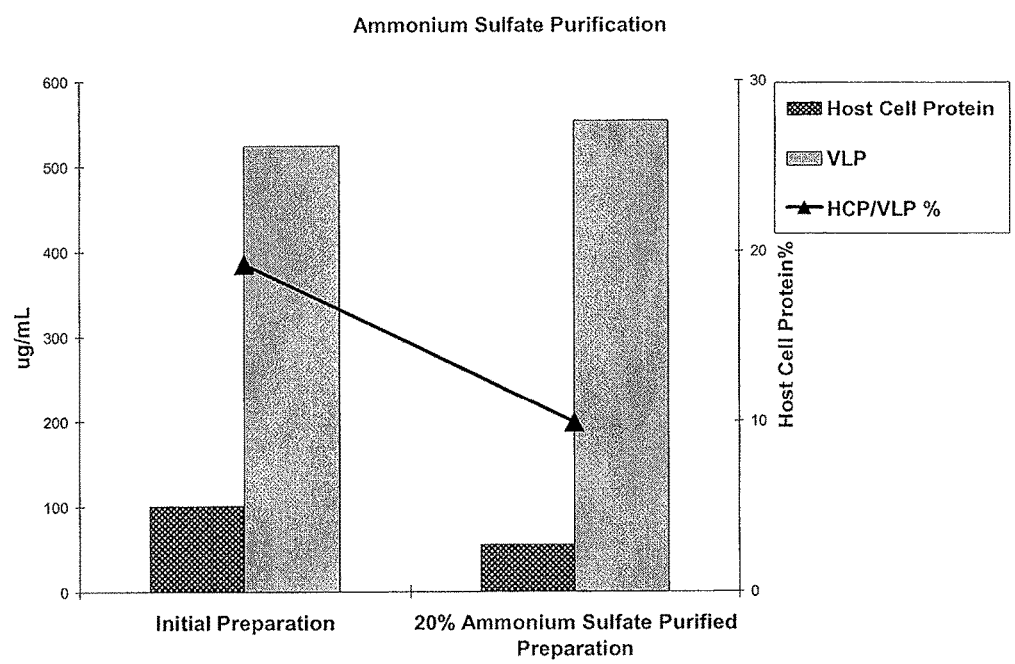
FIG. 21. Graph comparing the components of the initial Houston VLP preparation to the ammonium sulfate precipitated and redissolved material. Note the significant improvement in purity in the 20% ammonium sulfate preparation by the decrease in percent host cell protein to VLP (HCP/VLP %).
Figure 22:
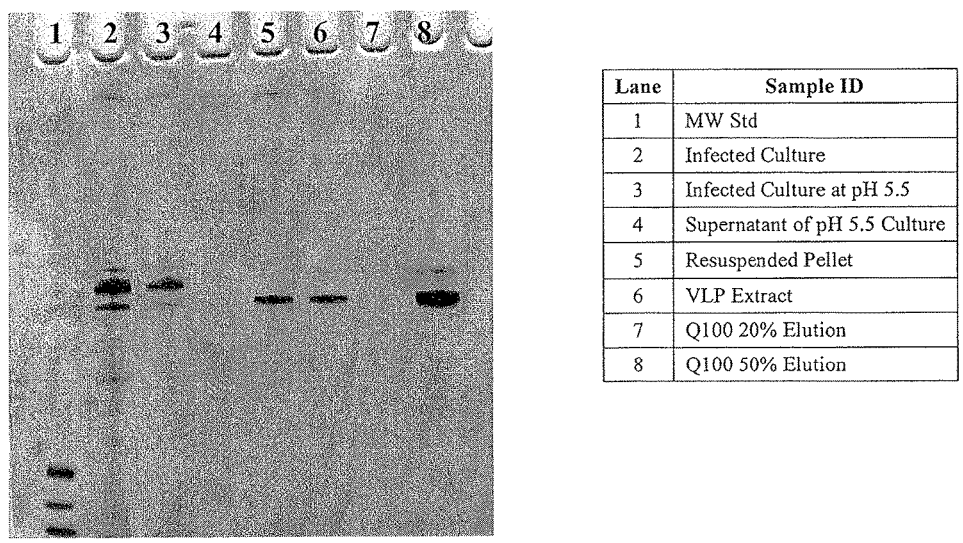
FIG. 22. Silver stained SDS-PAGE gel depicting purification process of Houston VLPs with precipitation followed by anion exchange chromatography. As shown by comparing lane 2 to lanes 5 and 6, precipitating the VLP with pH adjustment increases the purity. Lane 8 illustrates the ability of column chromatography to concentrate the VLPs.

Table 2 summarizes this purification process for the genogroup II Norovirus, Houston virus. FIGS. 14 and 15 provide the results from the cation exchange step, whereas FIGS. 16 and 17 provide the results from the methyl HIC chromatography step. FIGS. 18 and 19 provide an SDS-PAGE and HPLC-SEC of the purified Houston virus protein.

TABLE 2

| Culture Conditions | MOI = 1<br>3 × 10$^6$ cells/mL<br>Add NaCl to 150 mM on Day 7<br>Harvest the supernatant | |
|---|---|---|
| Purification Protocol | 1$^{st}$ step: Cation exchange SP FF resin | Equilibration Buffer: 20 mM citrate phosphate ph 4.0<br>Elution Buffer: 20 mM citrate phosphate, 1M sodium chloride pH 4.0 |

TABLE 2-continued

| | | |
|---|---|---|
| | | Step Gradient: $1^{st}$ step - wash with 20% elution buffer; $2^{nd}$ step - elution with 100% elution buffer |
| | $2^{nd}$ step: Methyl HIC resin - start material contains 15% ammonium sulfate | Equilibration Buffer: 100 mM sodium phosphate, 2.4M ammonium sulfate pH 6.8<br>Elution Buffer: 100 mM sodium phosphate pH 6.8<br>Sample loaded with the addition of ammonium sulfate to 15% (w/v).<br>Step Gradient: $1^{st}$ step - wash with 40% elution buffer; $2^{nd}$ step - elution with 70% elution buffer; $3^{rd}$ step - wash with 100% elution buffer. |
| | $3^{rd}$ step: Dialysis to buffer | Elution peak obtained from methyl HIC chromatography with 70% elution buffer dialyzed into 20 mM citrate phosphate buffer, 150 mM sodium chloride pH 6.0. |
| Final Yields | 20-30 mg purified protein/L | |

Figure 23:
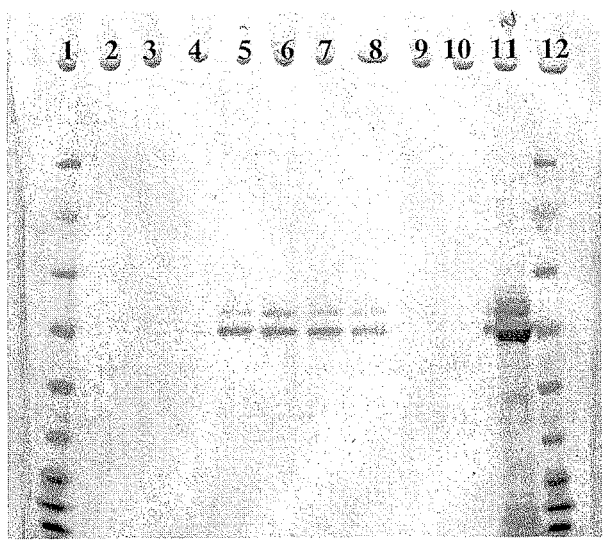
FIG. 23. Coomassie stained SDS-PAGE gel showing the purification process of Laurens VLPs with precipitation followed by anion exchange chromatography. A comparison of lanes 5 through 8 to lane 11 illustrates the increase in purity of Laurens VLP samples obtained with capture chromatography.

In addition to the process outlined in Table 2, we have been able to selectively precipitate Houston VLPs by decreasing the ionic strength of the conditioned media through the addition of deionized water. This offers a significant advantage because of the quick reduction in volume afforded by precipitation processes. Once precipitated, the VLPs can be separated using either centrifugation or filtration. Precipitated VLPs are then resuspended in an appropriate buffer and purified further using the chromatographic methods described above. We envision developing a scalable purification method using at least two and maybe all three of these chromatography techniques. The objective of this purification development would be to obtain a purification scheme that would provide functional VLPs that are identical in quality to the VLPs normally produced via ultracentrifugation and could be produced at large scale for commercial manufacture of the Houston VLPs. The preliminary data presented above demonstrate that chromatographic methods will be useful for purification of Houston virus VLPs. The VLPs were shown to bind to several resins and could also be eluted with the appropriate buffers. The next step in development will be to determine the combination and order in which these chromatographies will be used to produce a purer product. Also, additional experiments will be done to determine the modifications required to these chromatography techniques to obtain the maximum yield of VLPs. The finalized method will then be used in the large scale production and purification of Houston virus VLPs.

Example 3. Purification of G.II VLPs by Ammonium Sulfate Precipitation

A partially purified preparation of Houston VLPs was divided into 1 mL aliquots. Ammonium sulfate was added to each aliquot to achieve a final concentration of 10% to 35% (w/v). The samples were placed in a rotator and mixed end over end at 4° C. overnight. The samples were visually inspected for signs of precipitation. An aliquot of 20 µL, was removed and labeled “Amm suspension”. The ammonium sulfate suspension was centrifuged at 14,000×g for 10 min, room temperature. The resulting supernatant was pulled and labeled “Amm Supt”. The precipitated pellet was dissolved in a citrate buffer, pH 7.0, placed in a rotator and mixed end over end at 4° C. for 2 h. The samples were centrifuged at 14,000×g for 10 min. The resulting supernatant was pulled and labeled “Citrate supt”. FIG. 20 depicts a silver stained SDS-PAGE gel of samples taken at different points through the purification process. The two bands in the “Citrate supt” lane reflect the purified Houston VLPs.

The ammonium sulfate precipitation step significantly improved the purity of the VLPs as shown in FIG. 21. The percentage of host cell protein (HCP) to VLP protein was reduced by approximately half as a result of the ammonium sulfate precipitation.

Example 4. Purification of Norovirus Genogroup II VLPs by Precipitation Followed by Quaternary Amine (Q) Chromatography Houston VLP Purification Process A 1 liter suspension culture of SF9 cells was grown up to a density of $1.7\times10^7$ cells/mL and infected at a MOI (multiplicity of infection) of 0.5 pfu/cell with recombinant Baculovirus stock encoding for the Houston VP1 sequence. The infection was allowed to proceed to a viability of less than 20% (FIG. 22, lane 2). The Houston VLPs were harvested, purified, and concentrated in the following manner. The pH of the culture was lowered to 5.5 using HCl (lane 3) to precipitate the VLPs. Then the culture at pH 5.5 was centrifuged at 1,000×g for 5 minutes at room temperature. The supernatant (lane 4) was decanted and discarded. Next, the remaining pellet was resuspended in 20 mM Tris, 50 mM NaCl, 10 mM EDTA, at pH 8 (lane 5). The resuspended pellet was then centrifuged at 1,000×g for 5 minutes. The supernatant was decanted and labeled “Houston VLP extract” (lane 6). The precipitation process resulted in a significant improvement in purity as illustrated by the single band in lane 6 as compared to the multiple bands observed in the starting material in lane 2 (FIG. 22).

Following harvest, the Houston VLP extract was diluted 1:2 with water and loaded onto a Q100 membrane. The mobile phase buffer was 20 mM Tris pH 6.5 and the elution buffer was 20 mM Tris, 1M NaCl pH 6.5. After loading, the column was washed with 20% elution buffer (FIG. 22, lane 7) followed by 50% elution buffer (lane 8). The silver stained SDS-PAGE gel depicted in FIG. 22 shows that the Houston VLPs are concentrated by this capture chromatography step (compare lane 8 to lane 2).

Laurens VLP Purification Process

The VLP harvest process outlined above for the Houston VLPs was applied to a SF9 culture infected with recombinant Baculovirus stock encoding for the VP1 sequence from the GII.4 Laurens virus, resulting in a Laurens VLP extract (FIG. 23, lane 11). The resuspended pellet was diluted 1:2 with water and loaded onto a Q100 membrane. The mobile phase buffer was 20 mM Tris pH 6.8 and the elution buffer was 20 mM Tris, 1M NaCl pH 6.8. Lanes 2 through 10 of FIG. 23 illustrate the fractions collected over a step gradient elution from the Q100 membrane. The VLPs eluted in the 40% elution buffer fractions (lanes 5-8). As observed with Houston, the Laurens VLPs could be purified and concentrated using pH adjustment and capture chromatography.

Example 5. pH-Dependent Changes in Norovirus GI and GIII VLP Structure

To further optimize VLP purification procedures, the stability of VLPs from Norovirus GI and GII strains were exposed to pH ranges from around pH 2 to around pH 10.

Intact VLPs are of approximately 10 MDa mass. Intact VLPs exposed to certain pH conditions and analyzed by size exclusion high performance liquid chromatography (SE-HPLC) show a transition to a stable intermediate fragment with a mass of around 220 kDa relative to globular protein size standards. Fully denaturing conditions cause further disassembly of the intermediate fragment to the monomer of around 60 kDa. To further explore the pH range in which the Norovirus VLPs would remain intact, the pH of solutions containing either Norovirus GI VLPs or Norovirus GII VLPs was adjusted incrementally from about 2 to about 10 prior to analysis with SE-HPLC. Additionally, the SE-HPLC column buffer was adjusted to the same pH for analysis.

Figure 24A:
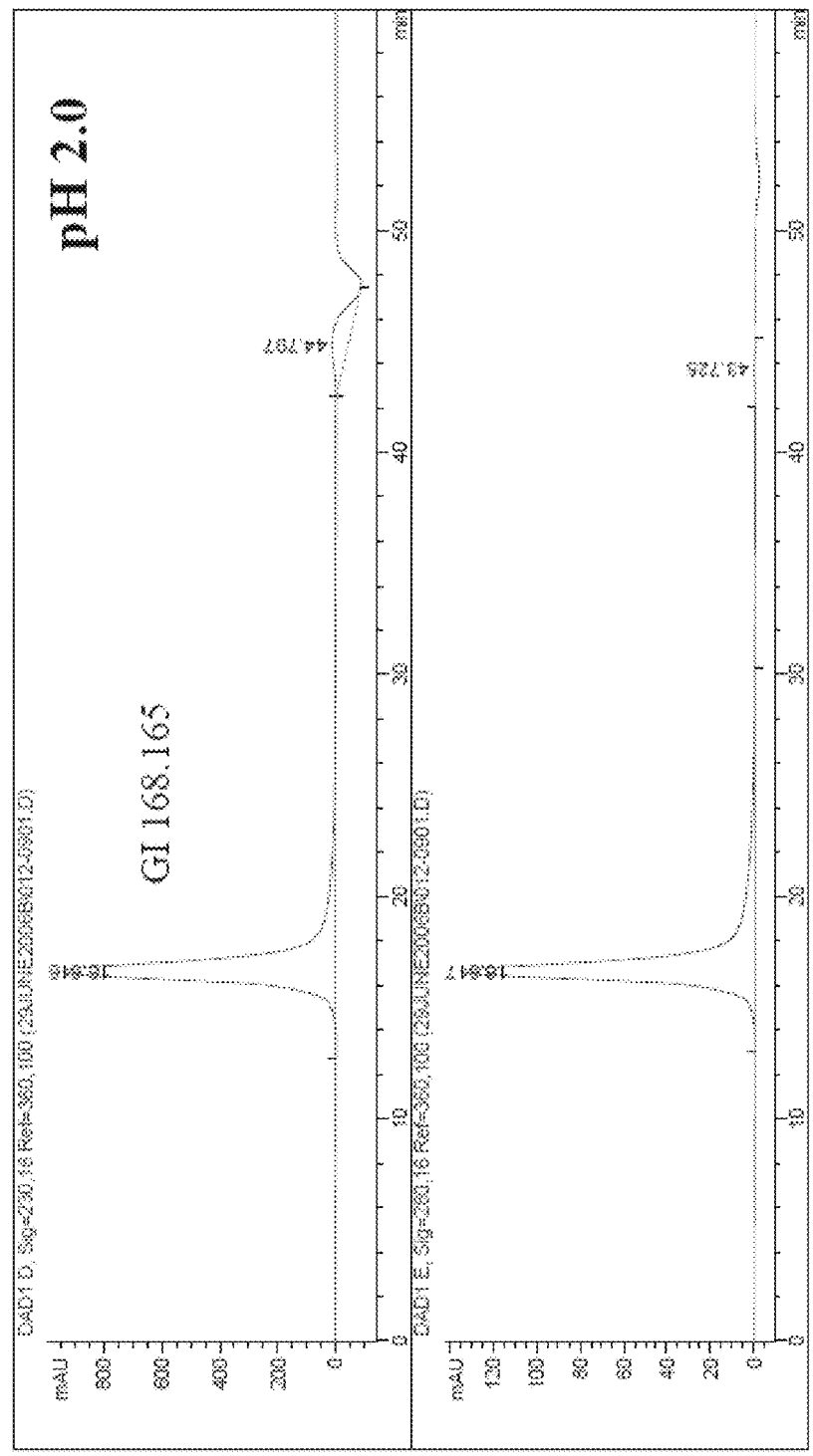
FIG. 24. SE-HPLC analysis of GI Norovirus VLPs at various pH values. Panel A. SE-HPLC analysis of GI Norovirus VLPs at pH 2. The absorbance peak at about 17 min corresponds to elution of intact, monodisperse VLPs. Panel B. SE-HPLC analysis of Norovirus GI VLPs at pH 8. The absorbance peak at about 16 min corresponds to elution of intact, monodisperse VLPs. Panel C. SE-HPLC analysis of Norovirus GI VLPs at pH 8.5. The absorbance peak at about 33 min corresponds to elution of the stable intermediate fragment of the VLP. Chromatograms show absorbance profiles at 230 nm (upper) and 280 nm (lower).
Figure 24B:
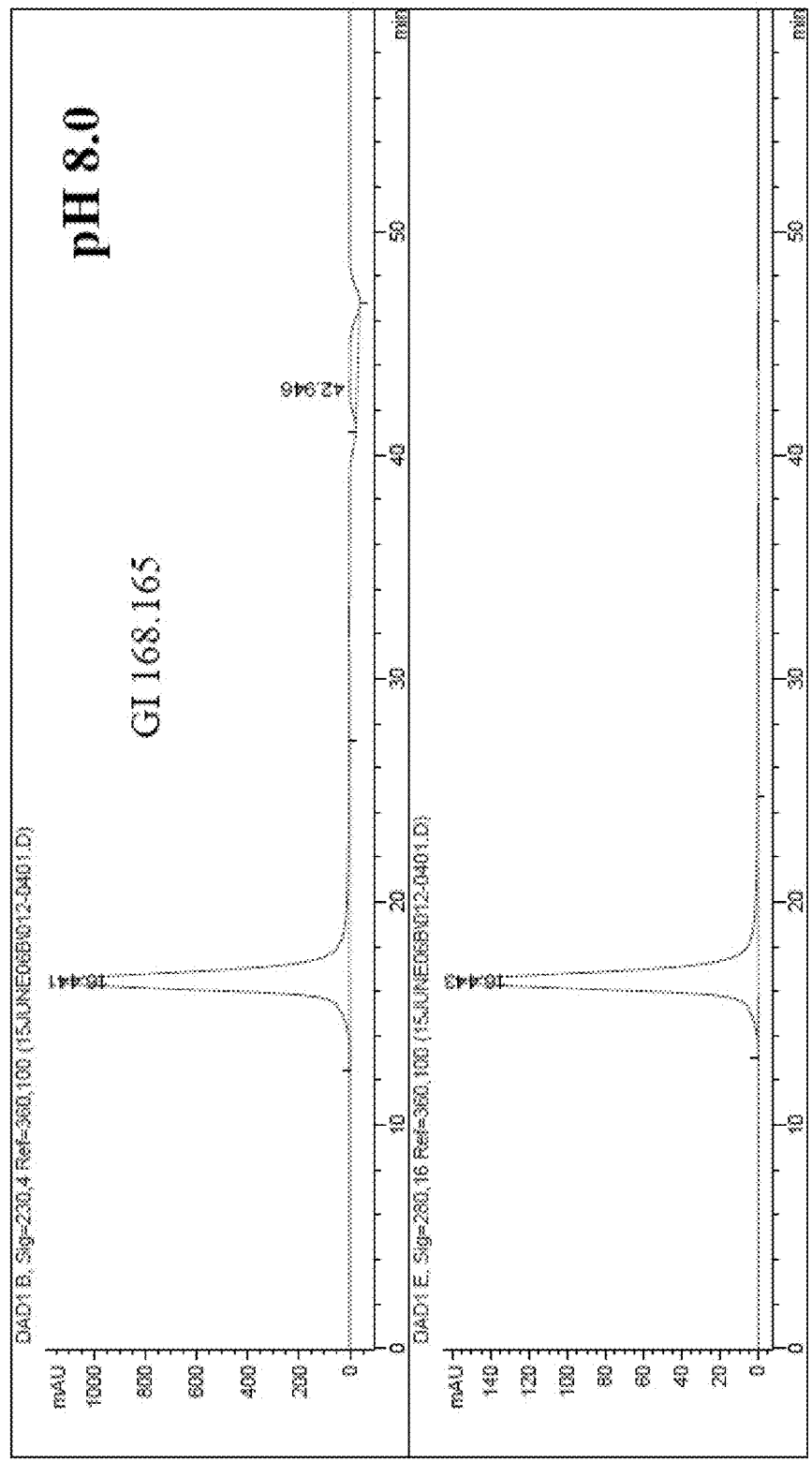
Figure 24C:
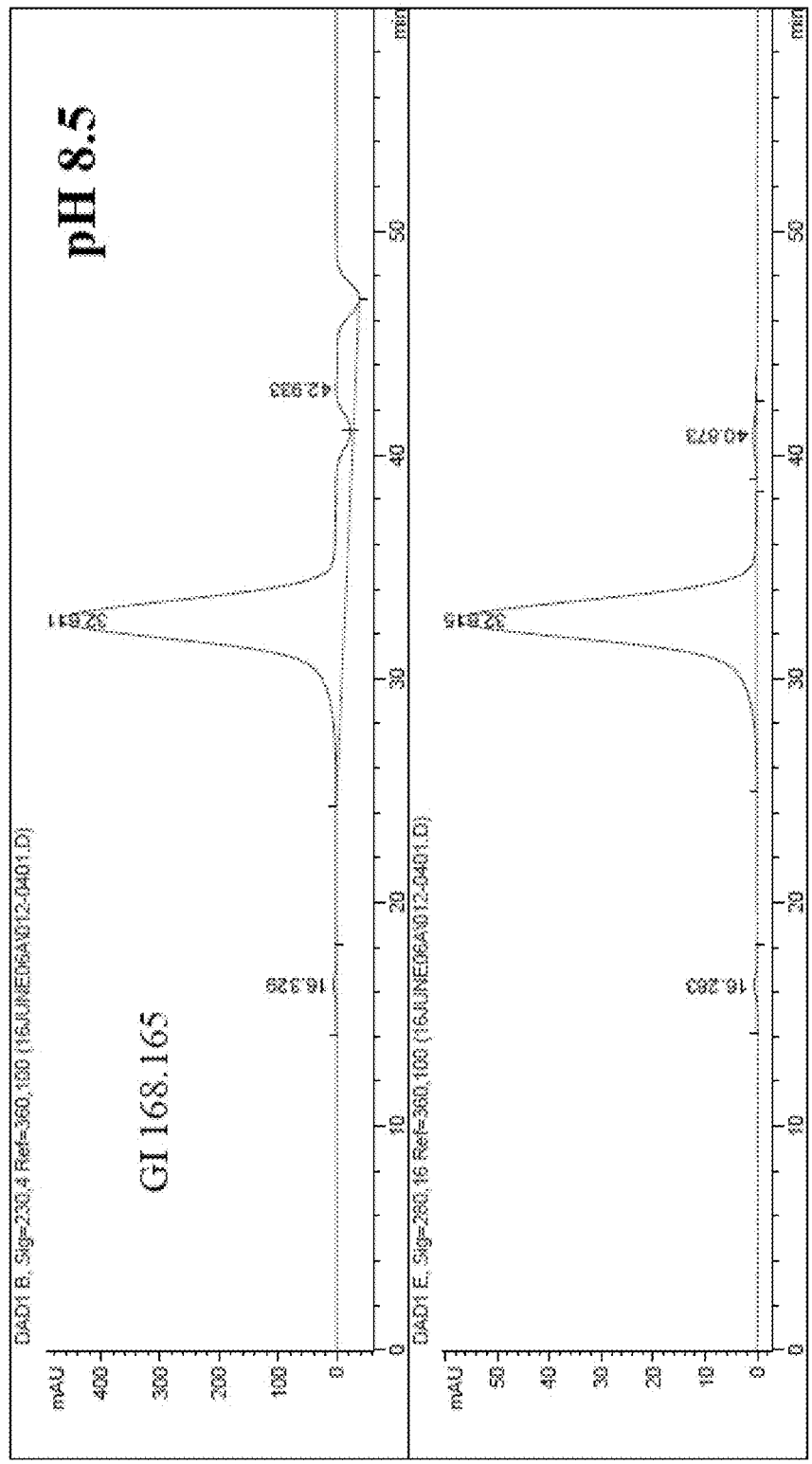

Norovirus GI VLPs exposed to pH conditions ranging from pH 2 (FIG. 24A) to pH 8 (FIG. 24B) exhibit a single absorbance peak at about 17 min representing intact, monodisperse VLPs. VLPs exposed to pH 8.5 (FIG. 24C) produce an absorbance peak at about 33 min, which represents the lower order stable intermediate VLP fragments. These results show that Norovirus GI VLPs remain intact from pH 2 to 8, and disassemble to the stable intermediate fragment between pH 8 and 8.5.

Figure 25A:
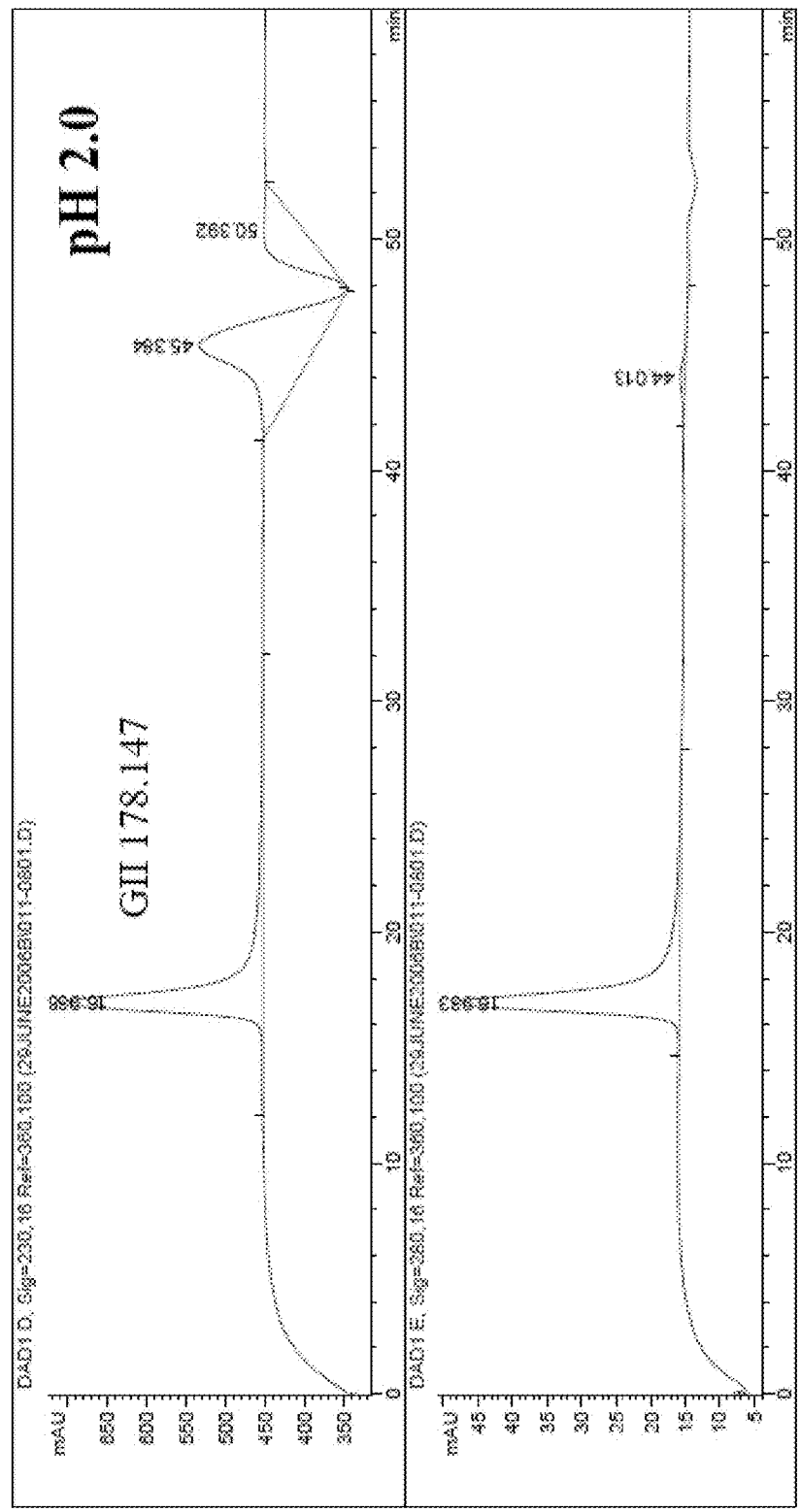
FIG. 25. SE-HPLC analysis of GII Norovirus VLP at various pH levels. Panel A. SE-HPLC analysis of GII Norovirus VLPs at pH 2. The absorbance peak at about 17 min corresponds to elution of intact, monodisperse VLPs. Panel B. SE-HPLC analysis of GII Norovirus VLPs at pH 9.5. The absorbance peak at about 17 min corresponds to elution of intact, monodisperse VLPs. Panel C. SE-HPLC analysis of GII Norovirus VLPs at pH 10. The absorbance peak at about 34 min corresponds to elution of the stable intermediate fragment of the VLP. Chromatograms show absorbance profiles at 230 nm (upper) and 280 nm (lower).
Figure 25B:
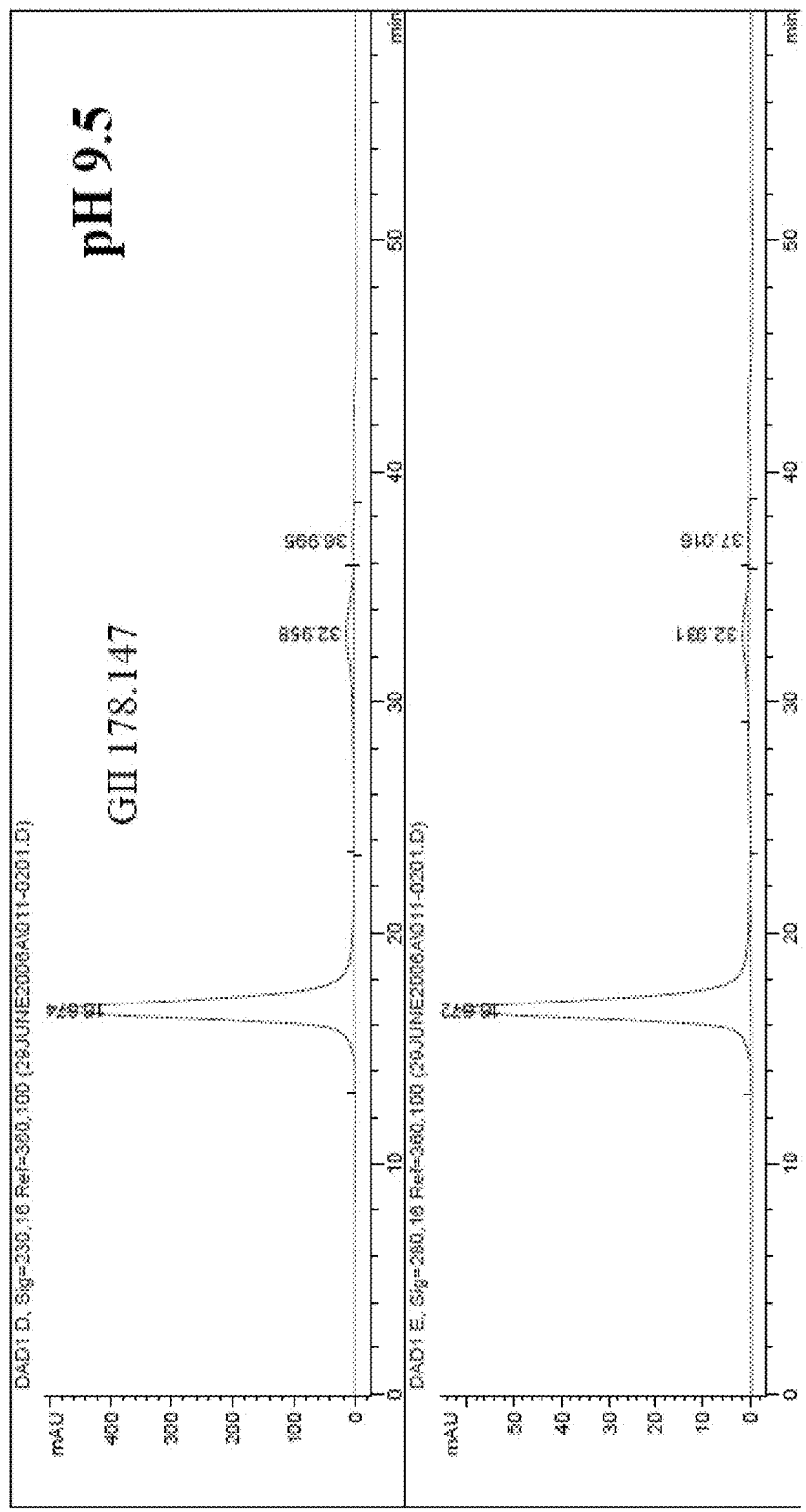
Figure 25C:
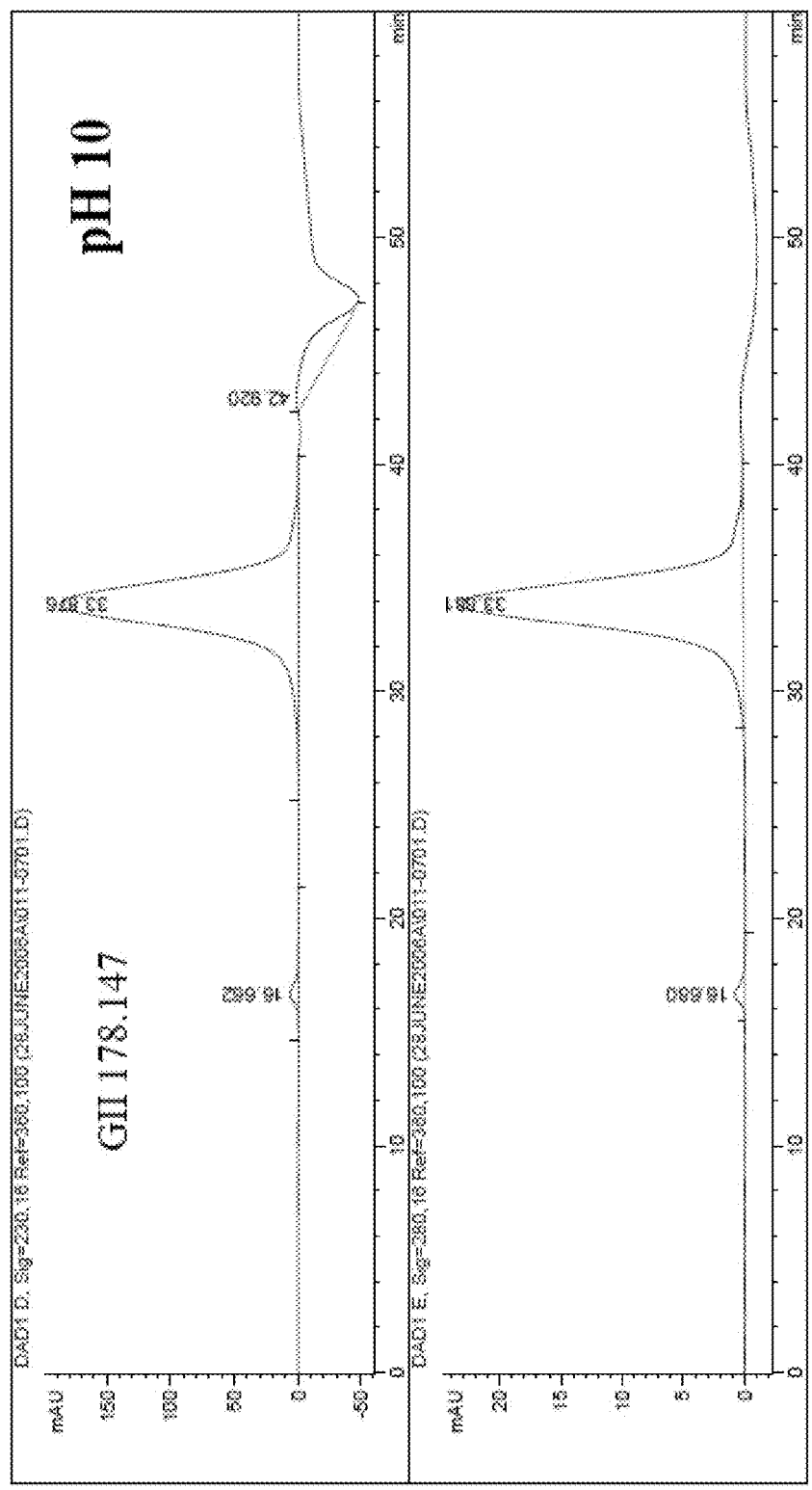

Norovirus GII VLPs exposed to pH conditions ranging from pH 2 (FIG. 25A) to pH 9.5 (FIG. 25B) produce single absorbance peaks at about 17 min, while VLPs exposed to pH 10 (FIG. 25C) exhibit single absorbance peaks around 34 min. Thus, these results show that Norovirus GII VLPs remain intact over the range of pH 2 to 9.5, and disassemble to the stable intermediate fragment between pH 9.5 and 10.

The findings of these experiments allow one to select conditions that result in intact VLPs or fragments thereof by adjusting the pH of the solution containing the VLPs. Such conditions may facilitate the purification process.

Example 6. Precipitation of VLP Proteins Using Polyethylene Glycol (PEG)

In a manner similar to that observed for the precipitation of VLPs by the addition of salt (Example 3), similar results may be produced by using other additives, such as polyethylene glycol, to cause the selective precipitation and solubilization of VLPs.

To determine the optimal concentration of polyethylene glycol (PEG) mass and concentration, PEG with molecular masses ranging from 200 to 20,000 is added to solutions containing VLPs in amounts that result in final PEG concentrations of 0 to 50% PEG in 5% increments. Following each 5% PEG addition, the VLP containing solutions are centrifuged at 10,000 g, and samples of the supernatants are obtained. The supernatant samples are subjected to SDS-PAGE, ELISA, and/or HPLC analyses to evaluate the purity and total concentration of the VLPs.

The VLPs will initially be found in the supernatant. As the PEG concentration increases, the VLPs and contaminating proteins will precipitate to varying degrees. When pellets are observed, the pellets are collected by decanting the supernatant. The pellet is resuspended in buffer and the purity of the VLPs analyzed by SDS-PAGE. The total VLP content in the resuspended pellets is evaluated by ELISA or HPLC. A table or graph of the relative purity of the supernate and pellet versus PEG mass and concentration is prepared. The optimal PEG mass and PEG concentration combination is selected based on the conditions resulting in the highest purity with acceptable yield or product recovery.

We claim:
1. A composition comprising Norovirus genogroup II, genotype 4 (GII.4) virus-like particles (VLPs), wherein the composition is prepared by a method comprising contacting a solution containing said VLPs with at least one chromatographic material, wherein the at least one chromatographic material is an anion exchange chromatographic material, wherein the chromatographic materials used in the method do not comprise hydroxyapatite, and wherein the VLPs are present in the composition at a purity level of greater than about 90%.
2. The composition of claim 1, wherein the anion exchange chromatographic material is a DEAE-Sepharose FF resin.
3. The composition of claim 1, wherein at least one chromatographic material comprises a cation exchange chromatographic material.
4. The composition of claim 1, wherein at least one chromatographic material comprises a hydrophobic interaction chromatographic material.
5. The composition of claim 1, wherein the method further comprises a precipitation step.
6. The composition of claim 5, wherein the precipitation step is a PEG precipitation step.
7. The composition of claim 6, wherein the solution containing the VLPs is subjected to the PEG precipitation step prior to contacting the solution containing the VLPs with the anion exchange chromatographic material.
8. The composition of claim 1, wherein the method further comprises an ultrafiltration and/or diafiltration step.
9. A pharmaceutical agent comprising the composition of claim 1.
10. The pharmaceutical agent of claim 9, wherein the pharmaceutical agent comprises a vaccine.
11. The composition of claim 1, wherein the VLPs are present in the composition at a purity level of greater than about 95%.

* * * * *